United States Patent [19]

Karjalainen et al.

[11] Patent Number: 4,689,339
[45] Date of Patent: Aug. 25, 1987

[54] 4-DIHYDROINDEN-2-YL-, 4-TETRAHYDRONAPHTH-2-YL-, AND 4-DIHYDROBENZOFURAN-2-YLIMIDAZOLES, USEFUL TO BLOCK $\alpha_2$-ADRENERGIC RECEPTORS

[75] Inventors: Arto J. Karjalainen, Oulu; Raimo E. Virtanen, Rusko; Arja L. Karjalainen; Kauko O. A. Kurkela, both of Oulu, all of Finland

[73] Assignee: Farmos Yhtyma oy, Turku, Finland

[21] Appl. No.: 800,192

[22] Filed: Nov. 21, 1985

[30] Foreign Application Priority Data

Nov. 23, 1984 [GB] United Kingdom ............... 8429578

[51] Int. Cl.[4] ................. A61K 31/415; C07D 233/64; C07D 405/04
[52] U.S. Cl. .................................. 514/396; 514/397; 548/336; 548/346
[58] Field of Search ............... 548/336, 346; 514/396, 514/397

[56] References Cited

U.S. PATENT DOCUMENTS 4,302,469 11/1981 Kluge et al. ............... 548/336
4,342,775 8/1982 Cozzi et al. ............... 548/336

FOREIGN PATENT DOCUMENTS

2933962A1 3/1981 Fed. Rep. of Germany ...... 548/340

OTHER PUBLICATIONS

Chemical Abstracts, vol. 101, 16791y, 1984.
α-Adrenoreceptor Reagents, 2, Effects of Modiciation of the 1,4-Benzodioxan Ring System on α-Adrenoreceptor Activity, Chapleo et al.; J. Med. Chem. 1984, vol. 27, pp. 570-576.

*Primary Examiner*—Richard A. Schwartz
*Assistant Examiner*—Kurt G. Briscoe
*Attorney, Agent, or Firm*—Armstrong, Nikaido, Marmelstein & Kubovcik

[57] ABSTRACT

A process for the preparation of a substituted imidazole of the formula

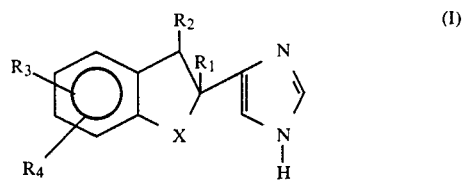

wherein X is —$CH_2$—, —$CH_2CH_2$— or —O— $R_1$ is H, lower alkyl or lower alkenyl, $OCH_3$ or $OCH_2CH_3$, $R_2$ is H, $CH_3$, $CH_2CH_3$, $OCH_3$ or OH, $R_3$ is H, $CH_3$, $CH_2CH_3$, $OCH_3$ or Hal, $R_4$ is H, $CH_3$, $CH_2CH_3$, $OCH_3$ or Hal, and Hal is halogen and their non-toxic acid addition salts exhibit valuable pharmacological activity and are useful especially as selective $\alpha_2$-receptor antagonists.

28 Claims, No Drawings

4-DIHYDROINDEN-2-YL-, 4-TETRAHYDRONAPHTH-2-YL-, AND 4-DIHYDROBENZOFURAN-2-YLIMIDAZOLES, USEFUL TO BLOCK $\alpha_2$-ADRENERGIC RECEPTORS The present invention relates to 4(5)-substituted imidazole derivatives and their non-toxic salts, and their preparation and use.

The imidazole derivatives of this invention are new potent and selective $\alpha_2$-receptor antagonists of the formula:

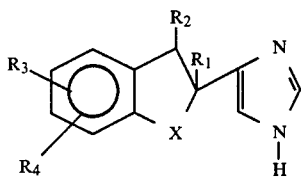

wherein X is —CH$_2$—, —CH$_2$CH$_2$— or —O—, R$_1$ is H, alkyl of 1 to 4 carbon atoms, alkenyl of 2 to 4 carbon atoms, OCH$_3$ or OCH$_2$CH$_3$, R$_2$ is H, CH$_3$, CH$_2$CH$_3$, OCH$_3$ or OH, R$_3$ is H, CH$_3$, CH$_2$CH$_3$, OCH$_3$ or Hal, R$_4$ is H, CH$_3$, CH$_2$CH$_3$, OCH$_3$ or Hal, and Hal is halogen, and their non-toxic pharmaceutically acceptable acid addition salts.

The compounds of the formula (I) form acid addition salts with both organic and inorganic acids. They can thus form any pharmaceutically usable acid addition salts, as, for instance, chlorides, bromides, sulfates, nitrates, phosphates, sulfonates, formates, tartrates, maleates, citrates, benzoates, salicylates, ascorbates and the like. The invention includes within its scope pharmaceutical compositions comprising at least one of the compounds of formula (1) or a non-toxic, pharmaceutically acceptable salt thereof, and a compatible pharmaceutically acceptable carrier therefor.

Adrenergic receptors are physiologically active binding sites which are specific to noradrenaline and adrenaline and located on the surface of the cell membrane. The adrenoceptors of the sympathetic nervous system have been classified into two different subtypes, namely alpha-($\alpha$) and beta-($\beta$) receptors which can both be further divided into two subgroups, i.e. $\alpha_1$ and $\alpha_2$ as well as $\beta_1$ and $\beta_2$. Of these receptor types, B$_1$, B$_2$ and $\alpha_1$ are mainly located postsynaptically on the surface of, e.g., smooth muscles and thus mediate, e.g., smooth muscle contraction or relaxation; whereas $\alpha_2$ receptors are mainly located presynaptically on the terminals of noradrenergic nerves. If $\alpha_2$ receptors are stimulated by noradrenaline under physiological conditions, noradrenaline release is blocked, i.e. there is a negative feed-back phenomenon.

As well as by noradrenaline itself, this negative feed-back phenomenon may be induced by certain synthetic $\alpha_2$-agonists like detomidine (compound A) and some of its near derivatives. The primary pharmacodynamic effects of detomidine, e.g. sedation, have also been proved to be due to its ability to stimulate $\alpha_2$-receptors (Virtanen et al., Progress in Neuro-Psychopharmacology and Biological Psychiatry, suppl. 1983. p. 308).

The compounds of formula (I) have valuable properties as antagonists to sedatives and analgetics used in veterinary medicine. Such veterinary medicines include, e.g., detomidine (compound A) and near derivatives thereof.

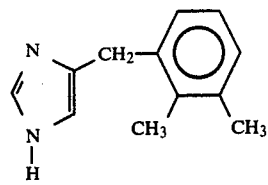

(detomidine)

Compound A has been disclosed in e.g. Eur. Pat. Appl. No. 24829.

Detomidine is used in veterinary medicine, especially in the handling of horses and cattle (pharmacological restraint), whereby the animal is sedated before investigation, treatment and difficult medical operations. Even a small surgical operation cannot be carried out without the use of a sedative agent.

When the treatment using detomidine has been completed, it is for practical reasons desirable to interrupt and restrain its effect by a specific antagonist or antidote. The animal can then immediately be transported away from the surgery, and expensive awakening rooms are not required. The ability of the animal to control its movements and co-ordination after awakening is improved. When animals are treated in cold surroundings this is absolutely necessary, because otherwise the animal will remain lying still for too long a time. When an awakening agent is used, the feeding of cattle can start more rapidly than otherwise. An interruption in feeding causes disturbances in production.

The use of an awakening agent in association with the use of detomidine saves time for the veterinarian as well as for the owner of the animal. The antidote makes practical the use of higher doses of detomidine, which induce a stronger analgetic effect. Thus, the safety of the treatment of big animals is increased. Without any awakening agent, detomidine cannot be used in some cases, as it is often not possible to wait until the animal has recovered from the influence of detomidine.

A selective $\alpha_2$-antagonist may also be predicted to be of use in some diseases which are believed to be connected with deficiency of noradrenalin available in the postsynaptic adrenoceptors of the central and/or peripheral nervous system. These diseases include, e.g., endogenic depression and asthma.

Glucose and lipid metabolisms are regulated by an inhibitory mechanism involving $\alpha_2$-receptors. Thus $\alpha_2$-antagonists may be significant in the treatment of metabolic diseases like diabetes and obesity.

Presynaptic $\alpha_2$-receptors also take part in platelet aggregation. It has been shown that $\alpha_2$-agonists activate and antagonists inhibit human platelet aggregation (Grand & Schutter, Nature 1979, 277, 659). Thus $\alpha_2$-antagonists may be useful clinically in pathogenic states involving increasing aggregation, e.g. migraine. The effects of ergotamine, a classical compound against migraine, are regarded as being due to its $\alpha_1$-agonist effect. Thus compounds with both antagonist effects of $\alpha_2$-receptors and agonist effects of postsynaptic $\alpha_1$-receptors may have great advantages in the acute and preventive treatment of migraine.

The compounds of the formula (I) can be prepared by the following processes:

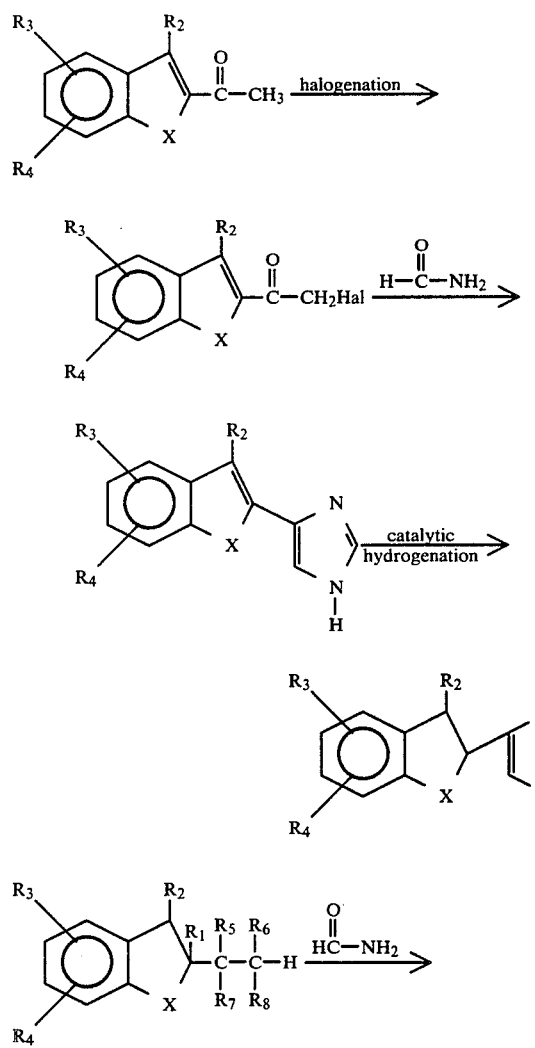

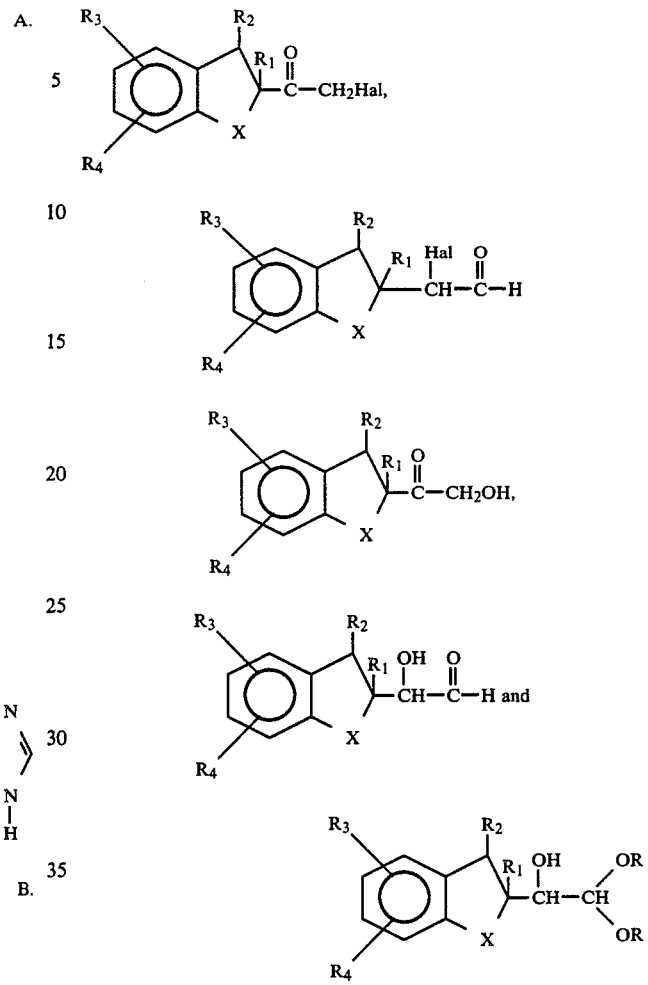

wherein each of $R_5$, $R_6$, $R_7$ and $R_8$ is hydrogen, hydroxy, halogen, amino, —O—alkyl containing 1 to 7 carbon atoms, or

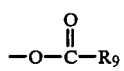

(wherein $R_9$ is an alkyl radical containing 1 to 7 carbon atoms or an aryl radical containing 6 to 10 carbon atoms); and wherein $R_5$ and $R_7$ can be combined to form a keto group, or $R_6$ and $R_8$ can be combined to form a keto group.

In process B, the following compounds can for example be used as starting materials:

A particularly convenient way to perform process B is the following (B1):

Another advantageous adaptation of process B is B2:

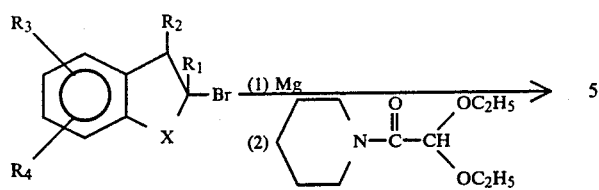
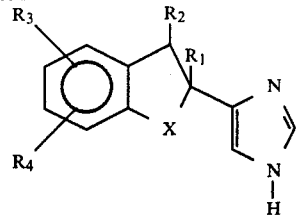
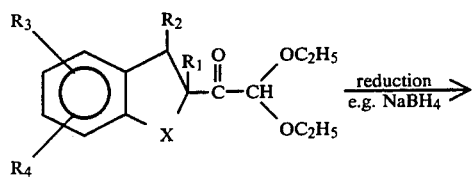
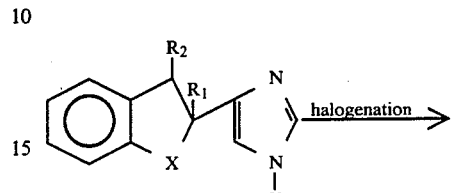
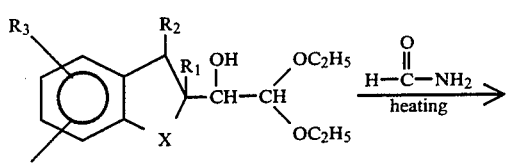
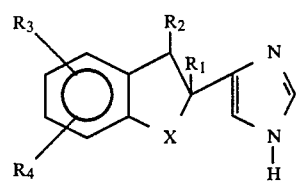
wherein $R_3$ is a halogen atom and $R_4$ is H or both $R_3$ and $R_4$ are halogens.
C.
D.
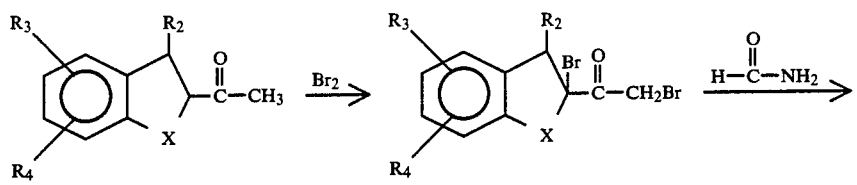
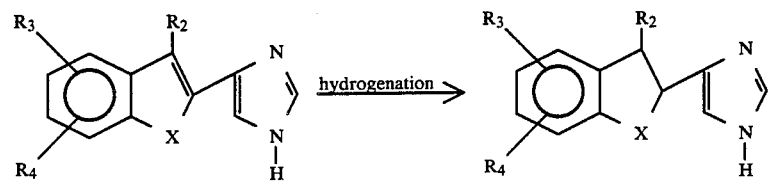
E.
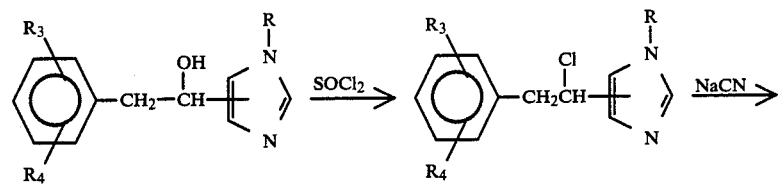
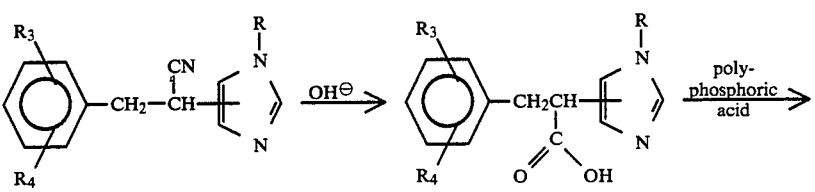

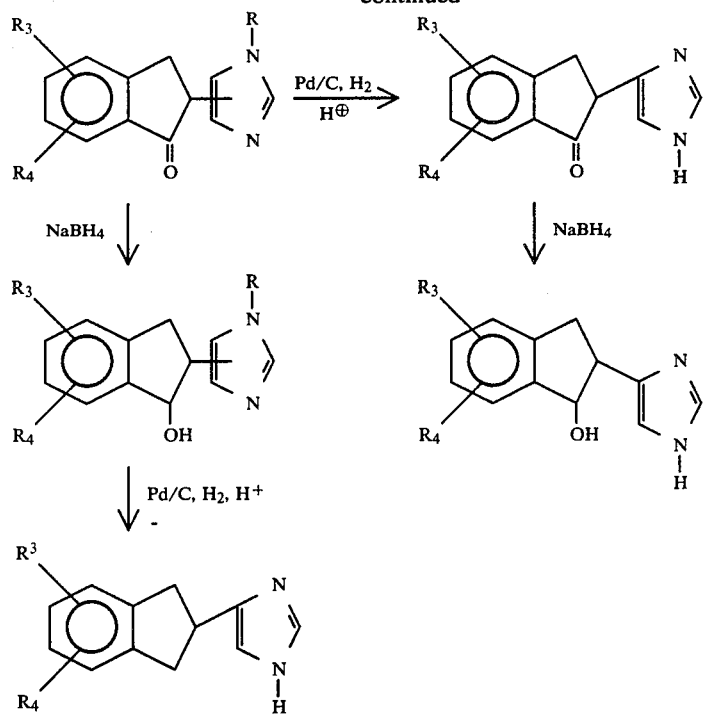
wherein R is a benzyl group.
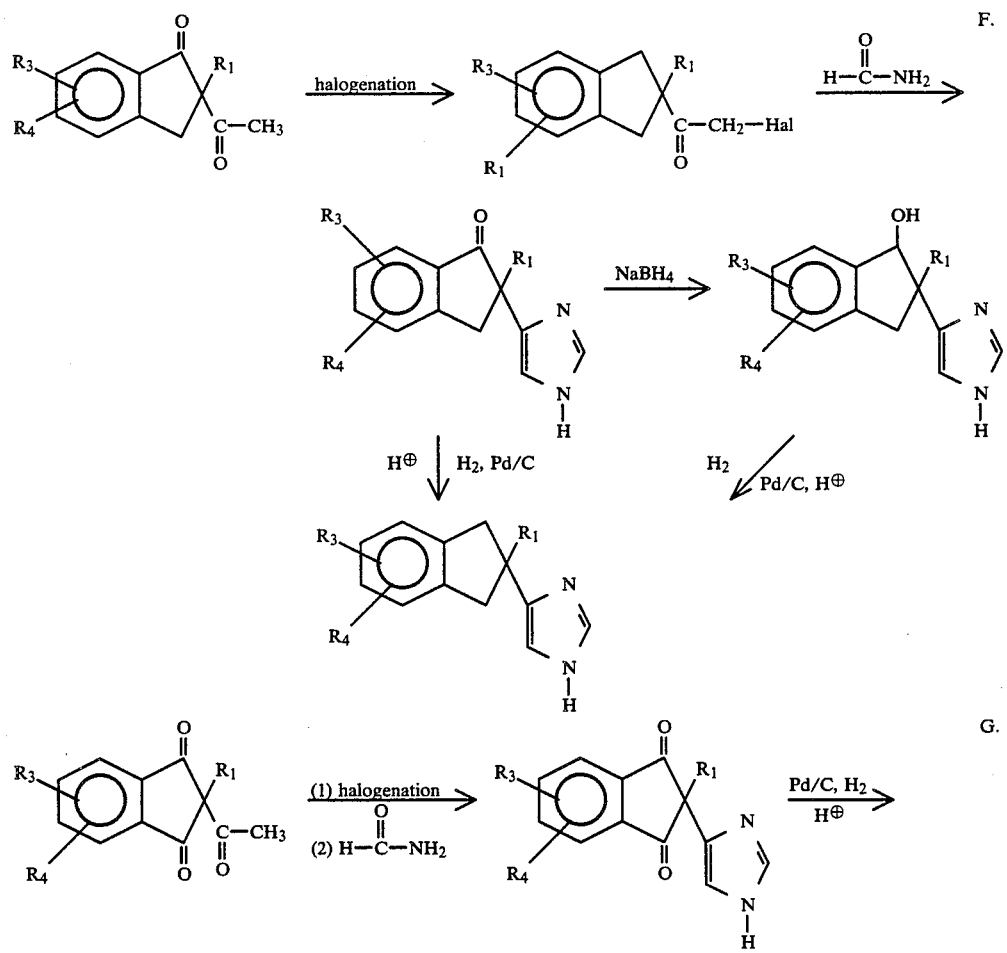

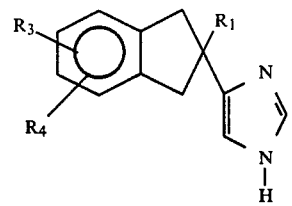

In process A the halogenation step can be performed by reaction with e.g. bromine in methylene chloride or diethyl ether with stirring at about 10° C.

In the second step the halogenated product and formamide are heated at 130°–200° C. for 3–8 hours.

The catalytic hydrogenation is performed in acidic water-ethanol mixture at about 70° C. at normal or elevated pressure using e.g. Pd/C as catalyst.

In process B1 the first and second steps are performed in the same way as the corresponding steps in process A.

Process B2. The Grignard reaction is carried out in an ether, e.g. tetra-hydrofuran or diethyl ether, at room temperature.

The reduction step is performed with e.g. sodium borohydride in ethanol at room temperature. The reaction with formamide is carried out as in A and B1, namely by heating at 130°–200° C. for 3–8 hours.

Process C. The halogenation is carried out with e.g. bromine in acidified water at about 10° C.

The following compounds of formula I are of special value as α2-antagonists:

Compound I

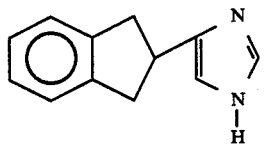

4(5)-(2,3-dihydro-1H—inden-2-yl)-imidazole

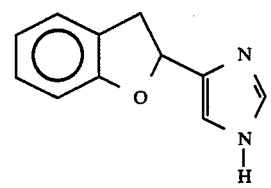

4(5)-(2,3-dihydrobenzofuran-2-yl)imidazole

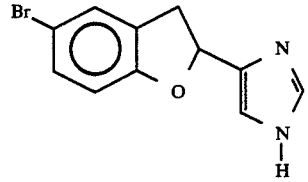

4(5)-(5-bromo-2,3-dihydrobenzofuran-2-yl)imidazole

Compound IV

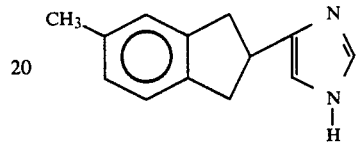

4(5)-(2,3-dihydro-5-methyl-1H—inden-2-yl)imidazole

Compound V

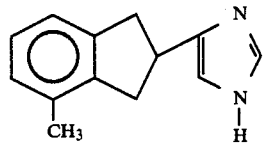

4(5)-(4-methyl-2,3-dihydro-1H—inden-2-yl)imidazole

Compound VI

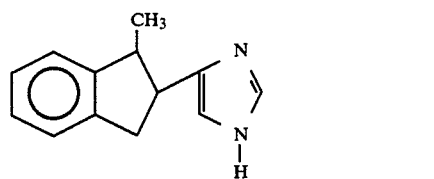

4(5)-(2,3-dihydro-1-methyl-1H—inden-2-yl)imidazole

Compound VII

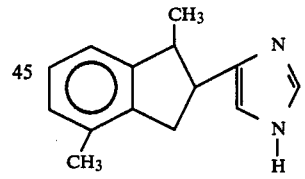

4(5)-(2,3-dihydro-1,4-dimethyl-1H—inden-2-yl)imidazole

Compound VIII

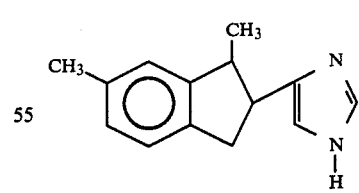

4(5)-(2,3-dihydro-1,6-dimethyl-1H—inden-2-yl)imidazole

Compound IX

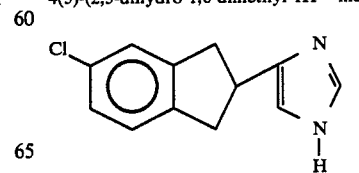

4(5)-(5-chloro-2,3-dihydro-1H—inden-2-yl)imidazole

-continued

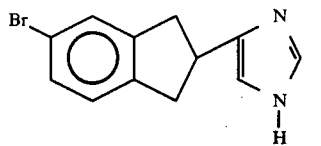
4(5)-(5-bromo-2,3-dihydro-1H—inden-2-yl)imidazole  Compound X

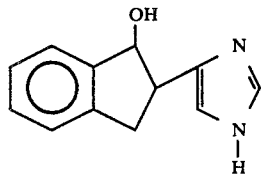
4(5)-(2,3-dihydro-1-hydroxy-1H—inden-2-yl)imidazole  Compound XI

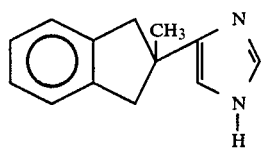
4(5)-(2,3-dihydro-2-methyl-1H—inden-2-yl)imidazole  Compound XII

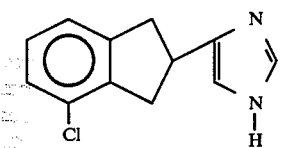
4(5)-(4-chloro-2,3-dihydro-1H—inden-2-yl)imidazole  Compound XIII

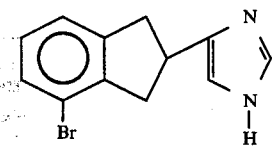
4(5)-(4-bromo-2,3-dihydro-1H—inden-2-yl)imidazole  Compound XIV

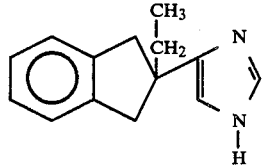
4(5)-(2,3-dihydro-2-ethyl-1H—inden-2-yl)imidazole  Compound XV

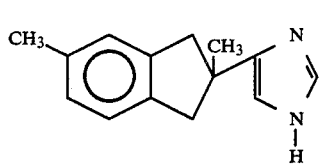
4(5)-(2,3-dihydro-2,5-dimethyl-1H—inden-2-yl)imidazole  Compound XVI

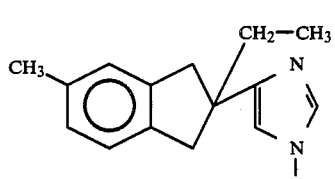
4(5)-(2,3-dihydro-2-ethyl-5-methyl-1H—inden-2-yl)imidazole  Compound XVII -continued

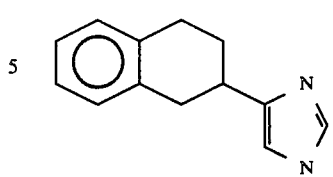
4(5)-(1,2,3,4-tetrahydronaphth-2-yl)imidazole  Compound XVIII

The pharmacological activity of the compounds of the present invention was determined as follows:

1. $\alpha_2$-antagonism in vitro $\alpha_2$-antagonism was determined by means of isolated, electrically stimulated mouse vas deferens preparation (Marshall et al., Br. J. Pharmac. 62, 147, 151, 1978). In this model, $\alpha_2$-agonist (detomidine) blocks electrically stimulated muscular contractions and the effect of the $\alpha_2$-antagonist is seen by administering it prior to the agonist and by determining its $pA_2$ value. Known $\alpha_2$-antagonists like yohimbine and rauwolscine were used as reference substances.

To obtain information also on the selectivity of the antagonist between $\alpha_1$- and $\alpha_2$-receptors, its ability to inhibit or stimulate $\alpha_1$-receptors was determined by means of isolated anococcygeus muscle (rat). The reference substances were now phenylephrine, a known $\alpha_1$-agonist, and prazosin, a known $\alpha_1$-antagonist. To determine $\alpha$-antagonism, muscular contraction was induced by phenylephrine and the $pA_2$ value of the studied compound was determined as above. $\alpha_1$-agonist effect is presented as the $pD_2$ value (negative logarithm of the molar concentration of the compound producing 50 percent of maximal contraction). Examples of the results are given in Table 1.

TABLE 1

| | $\alpha_2$-antagonism ($pA_2$ vs detomidine) mouse vas deferens | $\alpha_1$-antagonism ($pA_2$ vs phenylephrine) rat anococcygeus | $\alpha_1$-agonism ($pD_2$) rat anococcygeus |
|---|---|---|---|
| Compound I | 8.8 | — | 6.5 |
| Compound II | 7.5 | — | 5.5 |
| Compound III | 6.2 | — | 4.5 |
| Compound IV | 7.7 | — | 6.5 |
| Compound VI | 8.7 | — | 6.5 |
| Compound VII | 7.6 | — | 6.0 |
| Compound VIII | 7.6 | 5.9 | — |
| Compound XII | 8.1 | — | 5.5 |
| Compound XV | 8.3 | — | — |
| Compound XVII | 6.6 | — | — |
| Compound XVIII | 7.7 | — | 6.0 |
| Yohimbine | 8.1 | 6.6 | — |
| Rauwolscine | 8.1 | 6.3 | — |
| Prazosin | >5 | 9.0 | — |
| Phenylephrine | — | — | 6.5 |

2. $\alpha_2$-antagonism in vivo

The central $\alpha_2$-blocking effect of the studied substances under in vivo conditions was studied using two methods. First, it is known that in the rat $\alpha_2$-agonists induce dilatation of the pupil (mydriasis) which effect is transmitted via $\alpha_2$-receptors of the central nervous system. In anaesthetized rat, a standard dose of detomidine was administered intravenously. Thereafter increasing doses of the studied antagonist were injected intravenously and the reversal of detomidine-induced mydriasis was followed. The ED50 value of the antagonist, i.e. the dose producing a 50 percent reversal, was determined. Examples of the results of this test are presented in Table 2.

TABLE 2

| Compound | ED$_{50}$ (μg/kg iv) |
| --- | --- |
| I | 3 |
| II | 70 |
| III | 320 |
| IV | 20 |
| VI | 100 |
| VII | 100 |
| VIII | 100 |
| XII | 3 |
| XV | 6 |
| Yohimbine | 200 |
| Phentolamine | 1000 |
| Prazosin | >1000 |

α$_2$-antagonism in the central nervous system was secondly studied by following the ability of the antagonist to inhibit detomidine induced sedation in the mouse. This was done by measuring the increase of barbiturate sleeping time induced by detomidine. This effect of detomidine is known to be induced through α$_2$-receptor activation. The antagonist can be studied by administering it prior to detomidine. The results of the selected compounds are shown in Table 3.

TABLE 3

Effect of different antagonists (± percent of controls) on detomidine (150 μg/kg ip) induced potentiation of the barbiturate sleeping time in mice

| Dose mg/kg | Compound I | Compound II | yohimbine | prazosin |
| --- | --- | --- | --- | --- |
| 0.1 | −20 | −5 | 0 | 0 |
| 0.3 | −60 | −30 | −18 | 0 |
| 1 | −100 | −60 | −64 | 0 |
| 3 | not measured | −70 | −70 | +16 |
| 10 | not measured | −85 | −100 | +18 |

In the examples below, where $^1$H and $^{13}$C NMR spectrum shifts are presented, the NMR spectra were determined with a Bruker WB 80 DS apparatus using an internal tetramethylsilane standard, from which the presented chemical shifts (δ, ppm) are tabulated. The letters s, d, t and m are used to indicate a singlet, doublet, triplet or multiplet, respectively. In the same connection, the number of hydrogen atoms is also stated. The compounds which are indicated as bases are tested in deuterium methanol, deuterium acetone or deuterium chloroform, while the values for compounds which are indicated as hydrochlorides were determined in deuterium oxide or deuterium methanol. The mass spectra were determined with a Kratos MS 80 Autoconsole apparatus.

EXAMPLE 1

4(5)-(2,3-Dihydro-1H-inden-2-yl)imidazole

The 1-(2,3-dihydro-1H-inden-2-yl)ethanone used as the starting material can be obtained according to the publication (Carlson, G. L. B., Quina, F. H., Zarnegar, B. M. and Whitten, D. G., J. Am. Chem. Soc. 97 (1975) 347).

(a)

2-Bromo-1-(2,3-dihydro-1H-inden-2-yl)ethanone

Bromine (6.8 g) is slowly added to a stirred solution of 1-(2,3-dihydro-1H-inden-2-yl)ethanone (6.8 g) in 200 ml of dry ether, while keeping the temperature at +10° C. The rate of the addition of bromine is controlled so that the colour due to one added portion of bromine has been discharged before another portion is added. When the addition is complete, the ethereal solution is washed four times with 3M sodium carbonate solution, and is then washed three times with water. The ethereal solution is dried with anhydrous magnesium sulphate. After removal of the solvent the solid 2-bromo-1-(2,3-dihydro-1H-inden-2-yl)ethanone is obtained.

MS (m/z, % the relative intensity): 240 and 238 (8 and 12, M$^{+\cdot}$), 159 (47, M—Br), 145 (31, M—CH$_2$Br), 117 (73, M—COCH$_2$Br), 116 (78), 115 (100,

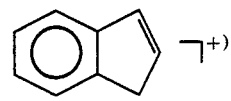

(b)

4(5)-(2,3-Dihydro-1H-inden-2-yl)imidazole

A mixture of 2-bromo-1-(2,3-dihydro-1H-inden-2-yl)ethanone (9.4 g) and formamide (140 ml) is heated at 170°–180° C. for 4 hours. Then the reaction mixture is allowed to cool to ambient temperature and poured into ice-cold, dilute hydrochloric acid solution. The mixture is washed twice with toluene. Then the aqueous layer is made alkaline with ammonia and extracted several times with ethyl acetate. The combined organic layers are dried over anhydrous magnesium sulfate and evaporated to dryness under reduced pressure. The oily residue, which contains the crude product to 4(5)-(2,3-dihydro-1H-inden-2-yl)imidazole is purified by flash chromatography (solvent system: methylene chloride-methanol 9.5:0.5). The 4(5)-(2,3-dihydro-1H-inden-2-yl)imidazole thus obtained is converted to its hydrochloride salt. The base is dissolved in ethyl acetate. Dry hydrogen chloride in ethyl acetate is added. The hydrochloride is precipitated with dry ether.

4(5)-(2,3-Dihydro-1H-inden-2-yl)imidazole hydrochloride

MS: 184 (100 M$^{+\cdot}$), 183 (71, M—H), 169 (89, M—CH$_3$), 156 (32), 150 (10), 147 (12), 142 (17), 141 (10), 139 (18), 129 (20), 128 (24), 127 (15), 119 (12), 116 (23), 115 (36), 111 (10), 91 (25), 77 (8), 69 (20).

$^1$H NMR (80 MHz, MeOH-d$_4$): 2.93–3.83 (5H, m, H$_2^1$, H$^2$ and H$_2^3$), 7.08–7.27 (4H, m, aromatic), 7.35 (1H, dd, im-5(4)), 8.83 (1H, d, $^4$J 1.37 Hz, im-2).

$^{13}$C NMR (20 MHz, MeOH-d$_4$): 36.80 (OFR d, C$_2$), 39,71 (2t, C$_1$ and C$_3$), 115.96 (d, im-5(4)), 125.32 (2d, aromatic), 127.86 (2d, aromatic), 134.85 (d, im-2), 138.76 (s, im-4(5)), 142.42 (2s, C$_8$ and C$_9$).

EXAMPLE 2

4(5)-(2,3-Dihydrobenzofuran-2-yl)imidazole (a)

1-(Benzofuran-2-yl)-2-bromoethanone

Benzofuran-2-yl methyl ketone (20 g) is dissolved in 100 ml of methylene chloride and 3.2 ml of bromine in methylene chloride is added at 5°–10° C. Then the reaction mixture is stirred at +15° C. for 2 hours. Then it is washed with water, with diluted sodium bicarbonate solution and again with water. The organic phase is dried and evaporated to dryness to give crude 1-(benzofuran-2-yl)-2-bromoethanone.

(b)

4(5)-(Benzofuran-2-yl)imidazole

The crude product from step (a) (12,1 g) and formamide (60 ml) are combined and heated at 170° C. for 5 hours. The reaction mixture is poured in water and concentrated hydrochloric acid added to make the mixture acidic. It is then washed with methylene chloride and the aqueous phase is made alkaline with sodium hydroxide. The product is extracted into methylene chloride which thereafter is washed with water, dried with sodium sulfate and evaporated in dryness. The residue consisting of crude product is converted to its hydrochloride salt in ethyl acetate. M.p. 229°–235° C.

$^1$H NMR (80 MHz, D$_2$O): 4.96 (2H, s), 6.77 (1H, s), 7.16–7.49 (6H, m), 8.46 (1H, s).

(c)

4(5)-(2,3-Dihydrobenzofuran-2-yl)imidazole

The product from step (b) (5 g) is dissolved in water (60 ml) and ethanol (30 ml) and concentrated hydrochloric acid (9 ml) is added. Then the reaction mixture is hydrogenated at 60° C. with 10% palladium on carbon as catalyst until no more hydrogen is consumed.

Then the catalyst is filtered and ethanol is distilled off. The aqueous solution is washed with methylene chloride and made alkaline with sodium hydroxide. The product is extracted into toluene. The toluene is washed with water and evaporated. The residue is crystallized from toluene-isopropanol and is then converted to its hydrochloride salt in isopropanol-ether. The yield is 1.3 g, m.p. 177°–178° C.

MS: 186 (46%), 185 (13%), 170 (15%), 169 (100%), 159 (5%), 158 (8%), 157 (7%), 146 (16%), 142 (43%), 131 (11%), 130 (20%), 103 (10%).

EXAMPLE 3

4(5)-(5-Bromo-2,3-dihydrobenzofuran-2-yl)imidazole

4(5)-(2,3-dihydrobenzofuran-2-yl)imidazole (0.6 g) and water (8 ml) are combined. Concentrated hydrochloric acid is added until the solution is acidic. Bromine (0.52 g) is added dropwise at about 10° C. and the mixture is stirred at this temperature for another half an hour. The precipitated product is filtered off and washed with water. The crude product is dissolved in warm water and the undissolved material filtered off. The filtrate is made alkaline and sodium hydroxide and the precipitate is filtered off. The product is converted to its hydrochloride salt in isopropanol-ether. The yield of 4-(5-bromo-2,3-dihydrobenzofuran-2-yl)imidazole hydrochloride is 0.4 g, m.p. 202°–204° C. M.p. of the base is 187°–188° C.

EXAMPLE 4 cis-4(5)-(2,3-Dihydro-1-methyl-1H-inden-2-yl)imidazole

The cis-2,3-dihydro-1-methyl-1H-indene-2-carboxylic acid used as the starting material can be obtained according to the literature (for example Shadbolt, R. S., *J. Chem. Soc.* (C), (1970) 920).

(a)

cis-2,3-Dihydro-1-methyl-1H-indene-2-carboxylic acid chloride cis-2,3-Dihydro-1-methyl-1H-indene-2-carboxylic acid (52.6 g) is converted to its acid chloride by treatment with thionyl chloride (130 ml). Excess thionyl chloride is distilled off and the acid chloride is distilled, b.p. 86°–89° C./0.45 mmHg. The yield is 47.9 g, 83%.

(b)

cis-1-(2,3-Dihydro-1-methyl-1H-inden-2-yl)ethanone cis-1-(2,3-Dihydro-1-methyl-1H-inden-2-yl)ethanone is prepared by the treatment of cis-2,3-dihydro-1-methyl-1H-indene-2-carboxylic acid chloride with ethoxymagnesiummalonic acid ethyl ester in dry ether and thereafter by the treatment of sulfuric acid according to the publication (Reynolds G. A. and Hauser, C. B., *Org. Synth.* 30 (1957) 70). The yield is 92%.

cis-1-(2,3-dihydro-1-methyl-1H-inden-2-yl)ethanone:

MS: 174 (31, M$^+$·), 159 (71, M—CH$_3$), 131 (38, M—COCH$_3$), 130 (100), 129 (27), 128 (21), 116 (24), 115 (54), 91 (33), 43 (16, C$^+$OCH$_3$).

$^1$H NMR (80 MHz, CDCl$_3$): 1.36 (3H, d, J 6.67 Hz, >CHCH$_3$), 2.24 (3H, s, COCH$_3$), 2.79–3.64 (4H, m, H$^1$, H$^2$ and H$_2{}^3$ of the indane ring), 7.17 (4H, s, aromatic).

$^{13}$C NMR (20 MHz, CDCl$_3$): δ19.60, 28.99, 34.80, 41.58, 61.05, 123.17, 124.13, 126.65, 126.71, 140.48, 146.38, 208.99.

(c)

2-Bromo-1-(2-bromo-2,3-dihydro-1-methyl-1H-inden-2-yl)ethanone

Bromine in methylene chloride is slowly added to a stirred solution of cis-1-(2,3-dihydro-1-methyl-1H-inden-2-yl)ethanone (34.8 g) in methylene chloride (835 ml), while keeping the temperature at +10° C. The reaction is followed by GLC. The first products are the isomers of 1-(2-bromo-2,3-dihydro-1-methyl-1H-inden-2-yl)ethanone and cis-2-bromo-1-(2,3-dihydro-1-methyl-1H-inden-2-yl)ethanone. When the added amount of bromine is about 0.3 mol, only the final product, 2-bromo-1-(2-bromo-2,3-dihydro1-methyl-1H-inden-2-yl)ethanone is visible in the chromatogram and the mono bromo products cannot be seen in the chromatogram any more. The methylene chloride solution is washed with water, then several times with the diluted NaHCO$_3$ solution and finally with water. The solvent is dried with Na$_2$SO$_4$ and evaporated to dryness.

2-bromo-1-(2-bromo-2,3-dihydro-1-methyl-1H-inden-2-yl)ethanone:

MS of the isomer a: 334, 332, 330 (0.5, 1, 0.5, M$^+$·), 253 and 251 (65 and 68, M—Br), 211 and 209 (1 and 1, M—COCH$_2$Br), 172 (11), 157 (28), 148 (26), 131 (15), 130 (80), 129 (93), 128 (79), 127 (30), 123 (22), 121 (23), 115 (100,

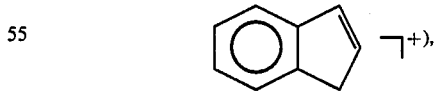

102 (10), 95 (14), 93 (14), 77 (11).

MS of the isomer b: M$^+$·invisible, 253 (65), 251 (69), 209 (1), 211 (1), 172 (17), 157 (38), 143 (28), 131 (14), 130 (69), 129 (100), 128 (85), 127 (35), 123 (18), 121 (18), 115 (95), 102 (11), 95 (13), 93 (14), 77 (12).

cis-2-bromo-1-(2,3-dihydro-1-methyl-1H-inden-2-yl)ethanone:

If the products are isolated, when 0.2 mol of bromine (instead of 0.3 mol) has been added, the following mixture of products is obtained: 1-(2-bromo-2,3-dihydro-1- methyl-1H-inden-2-yl)ethanone, cis-2-bromo-1-(2,3-dihydro-1-methyl-1H-inden-2-yl)ethanone and 2-bromo-1-(2-bromo-2,3-dihydro-1-methyl-1H-inden-2-yl)ethanone. Also a little amount of the starting compound can be seen in the chromatogram.

MS: M+· invisible, 173 (100, M—Br), 155 (12), 145 (26), 143 (10), 131 (31, M—COCH$_2$Br), 130 (16), 129 (29), 128 (26), 127 (14), 116 (29), 115 (59), 91 (28).

(d)

4(5)-(3-methyl-inden-2-yl)imidazole

2-Bromo-1-(2-bromo-2,3-dihydro-1-methyl-1H-inden-2-yl)ethanone (34.0 g) and formamide (520 ml) are combined and the mixture is heated with stirring at 170° C. for about 3 hours. The reaction mixture is cooled, then poured into water, made acidic with hydrochloric acid and washed with methylene chloride. The aqueous layer is then made alkaline with sodium hydroxide and the mixture is extracted with ethyl acetate. The organic extracts are washed with water and dried and evaporated to dryness. The residue, which consists of the crude product, is converted to the hydrochloride salt in ethyl acetate. After the recrystallization of the hydrochloride from isopropanol-ethanol the yield of the product is 11.4 g, 48% (m.p. 265°–268° C.).

The hydrochloride salt of 4(5)-(1-methyl-inden-2-yl)imidazole:

MS: 196 (100, M+·), 195 (44, M—H), 181 (30, M—CH$_3$), 168 (10), 167 (10), 141 (12), 139 (9), 127 (12), 115 (10), 98 (8), 97 (9).

$^1$H NMR (80 MHz, MeOH-d$_4$): δ2.34 (3H, t, $^5$J 2.22 Hz, CH$_3$), 3.75 (2H, q, $^5$J 2.22 Hz, >CH$_2$), 7.16–7.55 (4H, m, aromatic), 7.71 (1H, d, im-5(4)), 8.97 (1H, d, $^4$J 1.37 Hz, im-2).

$^{13}$C NMR (20 MHz, MeOH-d$_4$): δ12.10 (OFR q), 40.16 (t), 116.81 (d), 120.75 (d), 124.56 (d), 126.04 (s), 127.19 (d), 127.74 (d), 131.49 (s), 134.79 (d), 141.06 (s), 143.30 (s), 146.63 (s).

(e)

4(5)-(2,3-Dihydro-1-methyl-1H-inden-2yl)imidazole

The crude product of 4(5)-(3-methyl-inden-2-yl)imidazole (3.3 g) is dissolved in water (40 ml)-ethanol (20 ml)-concentrated hydrochloric acid (6 ml) solution. Then 0.33 g of 10% Pd/C is added and the mixture is stirred vigorously under a hydrogen atmosphere at about 60° C. until no more hydrogen is consumed. The reaction mixture is then filtered and the filtrate is evaporated to a smaller volume. The acidic solution is washed with methylene chloride. The aqueous phase is then made alkaline and extracted with methylene chloride. The organic extracts are dried and evaporated in dryness. The crude cis-4(5)-(2,3-dihydro-1-methyl-1H-inden-2-yl)imidazole is purified by converting it into the hydrochloride salt in acetone-ethyl acetate. The melting point of the hydrochloride is 192°–194° C.

The hydrochloride salt of cis-4(5)-(2,3-dihydro-1-methyl-1H-inden-2-yl)imidazole:

MS: 198 (100, M+·), 197 (27, M—H), 183 (78, M—CH$_3$), 170 (14), 169 (43), 156 (17), 154 (18), 142 (11), 130 (36), 129 (24), 128 (27), 127 (15), 117 (14), 116 (12), 115 (44), 91 (25), 82 (17), 81 (30), 77 (11).

$^1$H NMR (80 MHz, MeOH-d$_4$): δ0.94 (3H, d, $^3$J 7.01 Hz, CH$_3$), 3.23–4.03 (4H, m, H$^1$, H$^2$ and H$_2$$^3$), 7.19–7.25 (5H, m, aromatic and im-5(4)), 8.85 (1H, d, $^4$J 1.37 Hz, im-2).

$^{13}$C NMR (20 MHz, DMSO-d$_6$): δ16.34 (OFR q), 34.41 (t), 39.23 (d), 41.95 (d), 115.73 (d), 123.66 (d), 124.08 (d), 126.50 (2d), 133.28 (d), 133.77 (s), 140.49 (s), 147.00 (s).

EXAMPLE 5 cis-4(5)-(2,3-Dihydro-1,6-dimethyl-1H-inden-2-yl)imidazole (a)

α-Acetyl-4-methylbenzenepropanoic acid ethyl ester

The starting material, α-acetyl-4-methylbenzenepropanoic acid ethyl ester can be prepared for example according to the publication by L. Borowiecki and A. Kazubski (*Pol. J. Chem.* 52 (1978) 1447). Yield 60%, b.p. 120°–150° C./0.15 mmHg.

α-Acetyl-4-methylbenzenepropanoic acid ethyl ester:
$^1$H NMR (80 MHz, CDCl$_3$): δ1.20 (3H, t, J 7.18 Hz, CH$_2$CH$_3$), 2.17 (3H, s, CH$_3$CO or ArCH$_3$), 2.29 (3H, s, ArCH$_3$ or CH$_3$CO), 3.11 (2H, distorted d, J$_{ab}$ 758 Hz, >CHCH$_2$—), 3.74 (1H, distorted t, J$_{ab}$ 7.58 Hz, >CHCH$_2$—), 4.14 (2H, q, J 7.18 Hz, CH$_2$CH$_3$), 7.06 (4H, s, aromatic).

$^{13}$C NMR (20 MHz, CDCl$_3$): δ13.91, 20.88, 29.35, 33.56, 61.23, 61.35, 128.49 (2), 129.10 (2), 134.97, 136.00, 169.00, 202.15.

(b)

3,5-Dimethyl-indene-2-carboxylic acid

The 1,6-dimethyl-indene-2-carboxylic acid can be prepared by the treatment of α-acetyl-4-methylbenzenepropanoic acid ethyl ester with sulfuric acid (Shadbolt, R. S., *J. Chem. Soc.* (C), (1970) 920). Recrystallization from ethanol, m.p. 174°–182° C. Yield 59%.

3,5-dimethyl-indene-2-carboxylic acid:
$^1$H NMR (80 MHz, DMSO-d$_6$): δ2.38 (3H, s, ArCH$_3$), 2.46 (3H, t, $^5$J 2.39 Hz, =

$\underset{|}{C^1{-}CH_3)}$, 3.53 (2H, q, $^5$J 2.39 Hz, CH$_2$), 6.68 (1H, broad s, COOH), 7.11–7.44 (3H, m, aromatic).

$^{13}$C NMR (20 MHz, DMSO-d$_6$): δ11.95 (OFR q), 20.97 (q), 38.14 (t), 121.33 (d), 123.51 (d), 128.20 (d), 130.59 (s), 135.59 (s), 140.07 (s), 145.06 (s), 149.60 (s), 166.49 (s).

(c)

3,5-Dimethyl-indene-2-carboxylic acid chloride 3,5-Dimethyl-indene-2-carboxylic acid (37.3 g) is converted to its acid chloride by treatment with thionyl chloride (580 ml). Excess thionyl chloride is distilled off. Yield 40.5 g, 99%.

(d)

1-(3,5-Dimethyl-inden-2-yl)ethanone 1-(3,5-Dimethyl-inden-2-yl)ethanone is prepared by the same procedure as cis-1-(2,3-dihydro-1-methyl-1H-inden-2-yl)ethanone in Example 4b. A mixture of dry ether and tetrahydrofuran is used as solvent. Yield 84%.

1-(1,6-Dimethyl-inden-2-yl)ethanone:
MS: 186 (68, M+·), 171 (35, M—CH$_3$), 144 (39), 143 (100, M—COCH$_3$), 142 (13), 141 (32), 129 (17), 128 (71), 127 (16), 115 (26), 43 (77, C+OCH$_3$).

¹H NMR (80 MHz, CDCl₃): δ2.41 (3H, s, ArCH₃ or COCH₃), 2.42 (3H, s, COCH₃ or ArCH₃), 2.51 (3H, t, ⁵J 2.39 Hz, =

3.61 (2H, q, ⁵J 2.39 Hz, CH₂), 7.11–7.41 (3H, m, aromatic).

¹³C NMR (20 MHz, CDCl₃): δ12.85 (OFR q), 21.39 (q), 30.02 (q), 38.80 (t), 122.02 (d), 123.62 (d), 129.01 (d), 136.36 (s), 137.82 (s), 140.24 (s), 145.60 (s), 149.87 (s), 196.49 (s).

(e)

2-Bromo-1-(1,6-dimethyl-1H-inden-2-yl)ethanone

Bromine (2.80 g) is added to 1-(3,5-dimethyl-inden-2-yl)ethanone (3.00 g) in dry ether (30 ml), while keeping the temperature at +10° C. The mixture is extracted with water, several times with the diluted NaHCO₃ solution, again with water, dried and evaporated under reduced pressure to afford the product (2.54 g, 59%).

2-bromo-1-(3,5-dimethyl-1H-inden-2-yl)ethanone:

MS: 266 and 264 (13 and 13, M⁺·), 185 (4, M—Br), 171 (100, M—CH₂Br), 157 (13), 143 (49, M—COCH₂Br), 142 (18), 141 (32), 128 (27), 115 (18).

(f)

4(5)-(1,6-Dimethyl-1H-inden-2-yl)imidazole

4(5)-(1,6-Dimethyl-1H-inden-2-yl)imidazole is prepared by the reaction of 2-bromo-1-(1,6-dimethyl-1H-inden-2-yl)ethanone (14.3 g) with formamide (130 ml) as described earlier in Example 4d. The crude base is purified by flash chromatography (solvent system: methylene chloride-methanol 9.5:0.5). The 4(5)-(1,6-dimethyl-1H-inden-2-yl)imidazole thus obtained is converted to its hydrochloride salt. The base is dissolved in ethyl acetate. After dry hydrogen chloride in ethyl acetate is added the hydrochloride salt precipitates.

The base of 4-(5)-(1,6-dimethyl-1H-inden-2-yl)imidazole:

¹H NMR (80 MHz, MeOH-d₄): δ2.28 (3H, t, ⁵J 2.05 Hz, =

2.38 (3H, s, ArCH₃), 3.64 (2H, q, ⁵J 2.05 Hz, CH₂), 6.91–7.33 (4H, m, aromatic and im-5(4)), 7.73 (1H, d, ⁴J 0.86 Hz, im-2).

The hydrochloride salt of 4(5)-(1,6-dimethyl-inden-2-yl)imidazole:

¹H NMR (80 MHz, MeOH-d₄): δ2.33 (3H, t, ⁵J 2.22 Hz, =

2.41 (3H, s, ArCH₃), 3.71 (2H, q, ⁵J 2.22 Hz, CH₂), 7.05–7.43 (3H, m, aromatic), 7.70 (1H, d, im-5(4)), 8.96 (1H, d, ⁴J 1.37 Hz, im-2).

(g)

cis-4(5)-(2,3-Dihydro-1,6-dimethyl-1H-inden-2-yl)imidazole

The hydrochloride salt of 4(5)-(1,6-dimethyl-inden-2-yl)imidazole (0.55 g) is dissolved in water (6 ml)-ethanol (3 ml)concentrated hydrochloric acid (4 ml) solution. Hydrogenation is performed as it is described in Example 4e. The cis-4(5)-(2,3-dihydro-1,6-dimethyl-1H-inden-2-yl)imidazole is converted into the hydrochloride salt in ethylacetate. The melting point of the hydrochloride salt is 192°–196° C.

The hydrochloride salt of cis-4(5)-(2,3-dihydro-1,6-dimethyl-1H-inden-2-yl)imidazole:

MS: 212 (100, M⁺·), 211 (25, M—H), 197 (73, M—CH₃), 183 (41), 170 (14), 168 (14), 144 (25), 141 (10), 131 (22), 129 (19), 128 (20), 115 (14), 98 (12), 91 (15).

¹H NMR (80 MHz, MeOH-d₄): δ0.93 (3H, d, J 7.01 Hz, >CHCH₃), 2.31 (3H, s, ArCH₃), 3.16–4.00 (4H, m, H¹, H² and H₂³), 6.96–7.12 (3H, m, aromatic), 7,24 (1H, broad s, im-5(4)), 8.85 (1H, d, ⁴J 1.37 Hz, im-2).

¹³C NMR (20 MHz, MeOH-d₄): δ16.49 (OFR q), 21.39 (q), 36.17 (t), 41.83 (d), 43.98 (d), 117.17 (d), 125.14 (d), 125.38 (d), 128.74 (d), 134.63 (d), 136.55 (s), 137.82 (s), 138.70 (s), 148.14 (s).

EXAMPLE 6 cis-4(5)-(2,3-Dihydro-1,4-dimethyl-1H-inden-2-yl)imidazole

Method A

(a)

δ-Acetyl-2-methylbenzenepropanoic acid ethyl ester

The starting material, α-acetyl-2-methylbenzenepropanoic acid ethyl ester can be prepared for example according to the publication by L. Borowiecki and A. Kazubski (Pol. J. Chem. 52 (1978) 1447). Yield 64%, b.p. 142°–152° C./1.5 mmHg.

α-acetyl-2-methylbenzenepropanoic acid ethyl ester:

¹H NMR (80 MHz, CDCl₃): δ1.19 (3H, t, J 7.18 Hz, CH₂CH₃), 2.18 (3H, s, CH₃CO or ArCH₃), 2.32 (3H, s, ArCH₃ or CH₃CO), 3.17 (2H, distorted d, J_{ab} 7.58 Hz, >CHCH₂—), 3.76 (1H, distorted t, J_{ab} 7.58 Hz, >CHCH₂—), 4.14 (2H, q, J 7.18 Hz, CH₂CH₃), 7.10 (4H, s, aromatic).

(b)

1,4-Dimethyl-indene-2-carboxylic acid

The 1,4-dimethyl-indene-2-carboxylic acid can be prepared by the treatment of α-acetyl-2-methylbenzenepropanoic acid ethyl ester with sulfuric acid (Shadbolt, R. S., J. Chem. Soc. (C), (1970) 920). Recrystallization from ethanol, m.p. 190°–193° C. Yield 61%.

1,4-dimethyl-indene-2-carboxylic acid:

¹H NMR (80 MHz, DMSO-d₆): δ2.33 (3H, s, ArCH₃), 2.46 (3H, t, ⁵J 2.39 Hz=

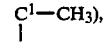

3.48 (2H, q, ⁵J 2.39 Hz, CH₂), 7.09–7.42 (4H, m, aromatic and —COOH).

¹³C NMR (20 MHz, DMSO-d₆): δ12.04 (OFR q), 17.86 (q), 37.44 (t), 118.51 (d), 126.68 (d), 128.26 (d), 130.11 (s), 132.71 (s), 141.67 (s), 144.42 (s), 149.81 (s), 166.43 (s).

(c)

1,4-Dimethyl-indene-2-carboxylic acid chloride 1,4-Dimethyl-indene-2-carboxylic acid is converted to its acid chloride by treatment with thionyl chloride. Yield 100%.

(d)

1-(1,4-Dimethyl-inden-2-yl)ethanone 1-(1,4-Dimethyl-inden-2-yl)ethanone is prepared by the same procedure as 1-(3,5-dimethyl-inden-2-yl)ethanone in Example 5d. Yield 75%.

1-(1,4-Dimethyl-inden-2-yl)ethanone:
MS: 186 (60, M+·), 171 (29, M—CH$_3$), 144 (33), 143 (100, M—COCH$_3$), 141 (27), 129 (18), 128 (66), 127 (15), 115 (28), 43 20(60, COCH$_3$).

$^1$H NMR (80 MHz, CDCl$_3$): δ2.38 (3H, s, ArCH$_3$ or COCH$_3$), 2.46 (3H, s, COCH$_3$ or ArCH$_3$), 2.53 (3H, t, $^5$J 2.39 Hz, =

3.55 (2H, q, $^5$J 2.39 Hz, CH$_2$), 7.10–7.46 (3H, m, aromatic).

$^{13}$C NMR (20 MHz, CDCl$_3$): δ13.13 (OFR q), 18.33 (q), 30.14 (q), 38.13 (t), 119.23 (d), 127.13 (d), 129.10 (d), 133.25 (s), 137.55 (s), 141.84 (s), 145.14 (s), 150.17 (s), 196.46 (s).

(e)

2-Bromo-1-(1,4-dimethyl-inden-2-yl)ethanone

2-Bromo-1-(1,4-dimethyl-inden-2-yl)ethanone is prepared by the same procedure as 2-bromo-1-(1,6-dimethyl-inden-2-yl)ethanone in Example 5e. Yield 45%.

2-bromo-1-(1,4-dimethyl-inden-2-yl)ethanone:
MS: 266 and 264 (14 and 15, M+·), 185 (3, M—Br), 171 (100, M—CH$_2$Br), 157 (13), 143 (M—COCH$_2$Br), 142 (18), 141 (33), 128 (32), 115 (21).

(f)

4(5)-(1,4-Dimethyl-inden-2-yl)imidazole

4(5)-(1,4-Dimethyl-inden-2-yl)imidazole is prepared by the reaction of 2-bromo-1-(1,4-dimethyl-inden-2-yl)ethanone (8.7 g) with formamide (330 ml) as described earlier in Example 4d. The product as base is extracted into methylene chloride. The yield of the base product is 3.0 g, 44%.

(g)

cis-4(5)-(2,3-Dihydro-1,4-dimethyl-1H-inden-2-yl)imidazole

The crude product of 4(5)-(1,4-dimethyl-inden-2-yl)imidazole (3.0 g) is dissolved in water (35 ml)-ethanol (18 ml)-concentrated hydrochloric acid (17.4 ml) solution. Then 0.30 g of 10% Pd/C is added and the mixture is stirred under a hydrogen atmosphere at about 60° C. until no more hydrogen is consumed. Work-up of the reaction mixture is as before in Example 4e. The crude imidazole derivatives is purified by flash chromatography (solvent system: methylene chloride/methanol 9.5/0.5). The cis-4(5)-(2,3-dihydro-1,4-dimethyl-1H-inden-2-yl)imidazole is converted into its hydrochloride salt in isopropanol/ethyl acetate and ether is added to precipitate the salt, m.p. 135°–140° C.

The hydrochloride salt of cis-4(5)-(2,3-dihydro-1,4-dimethyl-1H-inden-2-yl)imidazole:
MS: 212 (100, M+·), 211 (30, M—CH$_3$), 197 (80), 184 (13), 183 (34), 182 (11), 170 (13), 168 (16), 144 (35), 143 (10), 141 (11), 131 (14), 129 (15), 128 (12), 127 (10), 115 (17), 98 (16), 91 (15).

$^1$H NMR (80 MHz, MeOH-d$_4$): δ0.92 (3H, d, $^3$J 6.84 Hz, CH$_3$CH<), 2.31 (3H, s, ArCH$_3$), 3.14–4.01 (4H, m, H$^1$, H$^2$ and H$_2$$^3$), 6.98–7.09 (3H, m, aromatic), 7.28 (1H, broad s, im-5(4)), 8.83 (1H, d, $^4$J 1.37 Hz, im-2).

$^{13}$C NMR (20 MHz, MeOH-d$_4$): δ16.79 (OFR q), 19.06 (q), 34.95 (t), 41.13 (d), 44.16 (d), 117.20 (d), 122.14 (d), 128.25 (d), 128.77 (d), 134.67 (d), 134.88 (s), 136.49 (s), 140.30 (s), 147.87 (s).

Method B

(a)

cis-2,3-Dihydro-1,4-dimethyl-1H-indene-2-carboxylic acid 1,4-Dimethyl-indene-2-carboxylic acid (35.5 g) is hydrogenated in ethanol-water (700 ml–70 ml) over 10% palladium on carbon at ambient temperature. After filtration ethanol is evaporated. Water is added and the precipitated cis-2,3-dihydro-1,4-dimethyl-1H-indene-2-carboxylic acid is filrated. Yield 33.3 g, 93% M.p. 132°–135° C.

cis-2,3-Dihydro-1,4-dimethyl-1H-indene-2-carboxylic acid:
$^1$H NMR (80 MHz, DMSO-d$_6$): δ1.08 (3H, d, J 6.78 Hz, CH$_3$CH<), 2.20 (3H, s, ArCH$_3$), 2.70–3.67 (4H, m, H$^1$, H$^2$ and H$_2$$^3$), 6.88–7.08 (3H, m, aromatic), 12.15 (1H, broad s, —COOH).

$^{13}$C NMR (20 MHz, DMSO-d$_6$): δ16.95 (OFR q), 18.49 (q), 31.39 (t), 41.01 (d), 47.43 (d), 120.60 (d), 126,44 (d), 127.14 (d), 133.01 (s), 139.64 (s), 146.45 (s), 174.33 (s).

(b)

cis-2,3-Dihydro-1,4-dimethyl-1H-indene-2-carboxylic acid chloride cis-2,3-Dihydro-1,4-dimethyl-1H-indene-2-carboxylic acid is converted to its acid chloride by treatment with thionyl chloride. Yield 92%.

cis-2,3-dihydro-1,4-diemethyl-1H-indene-2-carboxylic acid chloride:
$^1$H NMR (80 MHz, CDCl$_3$): δ1.44 (3H, d, J 6.67 Hz, CH$_3$CH<), 2.25 (3H, s, ArCH$_3$), 2.84–4.02 (4H, m, H$^1$, H$^2$, H$_2$$^3$), 6.92–7.11 (3H, m, aromatic).

(c)

cis-1-(2,3-Dihydro-1,4-dimethyl-1H-inden-2-yl)ethanone 1-(2,3-Dihydro-1,4-dimethyl-1H-inden-2-yl)ethanone is prepared by the same procedure as 1-(2,3-dihydro-1-methyl-1H-inden-2-yl)ethanone in Example 4b. B.p. 181°–182° C./1 mmHg. Yield 55%.

cis-1-(2,3-dihydro-1,4-dimethyl-1H-inden-2-yl)ethanone:
$^1$H NMR (80 MHz, CDCl$_3$): δ1.37 (3H, d, $^3$J 6.65 Hz, CH$_3$CH<), 2.26 (6H, 2s, COCH$_3$ and ArCH$_3$), 2.85–3.72 (4H, m, H$^1$, H$^2$ and H$_2$$^3$ of the indane ring), 6.88–7.16 (3H, m, aromatic). $^{13}$C NMR (20 MHz, CDCl$_3$): δ18.82 (OFR q), 19.91 (q), 28.99 (q), 33.44 (t), 41.85 (d), 60.65 (d), 120.56 (d), 127.04 (d), 127.56 (d), 133.55 (s), 139.30 (s), 146.17 (s), 209.14 (s).

(d)

2-Bromo-1-(2-bromo-2,3-dihydro-1,4-dimethyl-1H-inden-2-yl)ethanone

Bromination of cis-1-(2,3-dihydro-1,4-dimethyl-1H-inden-2-yl)ethanone (11.78 g) is performed with bromine (10.00 g)/methylene chloride (40 ml) in methylene chloride (120 ml) as in the case of 1-(3,5-dimethyl-inden-2-yl)ethanone in Example 5e. Work-up of the reaction mixture gives the light yellow oil, which contains two isomers (a and b) of 2-bromo-1-(2-bromo-2,3-dihydro-1,4-dimethyl-1H-inden-2-yl)ethanone.

2-bromo-1-(2-bromo-2,3-dihydro-1,4-dimethyl-1H-inden-2-yl)ethanone:

MS of the isomer a: 348, 346, 344 (0.3, 0.5, 0.1, M$^{+\cdot}$), 267 and 265 (77 and 77, M—Br), 186 (10), 171 (18), 157 (18), 144 (64), 143 (74), 141 (23), 129 (74), 128 (100), 127 (29), 123 (16), 121 (16), 115 (24), 43 (13).

MS of the isomer b: 348, 346, 344 (all invisible, M$^{+\cdot}$), 267 and 265 (71 and 78, M—Br), 186 (18), 185 (16), 171 (38), 157 (24), 144 (52), 143 (91), 141 (32), 129 (73), 128 (100), 127 (30), 123 (12), 121 (13), 115 (36), 43 (15).

(e)

4(5)-(1,4-Dimethyl-inden-2-yl)imidazole

4(5)-(3,7-Dimethyl-inden-2-yl)imidazole is prepared from 2-bromo-1-(2-bromo-2,3-dihydro-1,4-dimethyl-1H-inden-2-yl)ethanone and formamide as described for 2-bromo-1-(2-bromo-2,3-dihydro-1-methyl-1H-inden-2-yl)ethanone in Example 4d.

(f)

cis-4(5)-(2,3-Dihydro-1,4-dimethyl-1H-inden-2-yl)imidazole cis-4(5)-(2,3-Dihydro-1,4-dimethyl-1H-inden-2-yl)imidazole is obtained in a similar manner as in method Ag.

EXAMPLE 7

4(5)-(2,3-Dihydro-2-methyl-1H-inden-2-yl)imidazole (a)

2,3-Dihydro-2-methyl-1H-indene-2-carboxylic acid 2,3-Dihydro-2-methyl-1H-indene-2-carboxylic acid can be prepared for example by the procedure of Huebner, C. F., Donoghue, E. M., Strachan, P. L., Beak, P. and Wenkert, E. (J. Org. Chem. 27 (1962) 4465) or by the reaction of lithium N-isopropylcyclohexylamide and methyl iodide (Rathke, M. V. and Lindert, A., J. Am. Chem. Soc. 93 (1971) 2318) with 2,3-dihydro-1H-indene-2-carboxylic acid methyl ester (prepared by the methylation of 2,3-dihydro-1H-indene-2-carboxylic acid in the presence of sulphuric acid) followed by hydrolysis.

2,3-dihydro-2-methyl-1H-indene-2-carboxylic acid:

$^1$H NMR (80 MHz, CDCl$_3$): δ1.40 (3H, s, CH$_3$), AB quartet: γA 2.84, γB 3.52, J$_{AB}$, 15.73 Hz (4H, 2x CH$_2$), 7.17 (4H, s, aromatic), about 9.3 (1H, broad s, COOH).

$^{13}$C NMR (20 MHz, CDCl$_3$): δ24.84 (OFR q, CH$_3$), 43.94 (2t, C$_1$ and C$_3$), 49.48 (s, C$_2$), 124.62 (2d, aromatic), 126.62 (2d, aromatic), 141.06 (2s, C$_8$ and C$_9$), 183.65 (s, CO).

(b)

2,3-Dihydro-2-methyl-1H-indene-2-carboxylic acid chloride

A stirred mixture of 2,3-dihydro-2-methyl-1H-indene-2-carboxylic acid (6.70 g) and thionyl chloride (70 ml) is heated under reflux for 14 hr. The ecess of thionyl chloride is removed and the acid chloride is distilled. Yield 5.35 g, 72%, bp. 93°-98° C./3 mmHg.

2,3-dihydro-2-methyl-1H-indene-2-carboxylic acid chloride:

$^1$H NMR (80 MHz, CDCl$_3$): δ1.51 (3H, s, CH$_3$), AB quartet: γA 2.91, γB 3.60, J$_{AB}$ 15.90 Hz (4H, 2x CH$_2$), 7.19 (4H, s, aromatic).

(c)

1-(2,3-Dihydro-2-methyl-1H-inden-2-yl)ethanone 1-(2,3-Dihydro-2-methyl-1H-inden-2-yl)ethanone is prepared from 2,3-dihydro-2-methyl-1H-indene-2-carboxylic acid chloride in the same way as it is described in Example 4b. Yield 75%.

1-(2,3-dihydro-2-methyl-1H-inden-2-yl)ethanone:

$^1$H NMR (80 MHz, CDCl$_3$): δ1.32 (3H, s, —>CCH$_3$), 2.20 (3H, s, COCH$_3$), AB quartet: γA 2.76, γB 3.39, J$_{AB}$ 15.73 Hz (4H, 2x CH$_2$), 7.17 (4H, s, aromatic).

(d)

2-Bromo-1-(2,3-dihydro-2-methyl-1H-inden-2-yl)ethanone 1-(2,3-Dihydro-2-methyl-1H-inden-2-yl)ethanone (3.69 g) in methylene chloride (40 ml) is stirred and cooled at 10° C. during the dropwise addition of bromine (2.82 g)/methylene chloride (10 ml). Work-up of the resultant solution gives 2-bromo-1-(2,3-dihydro-2-methyl-1H-inden-2-yl)ethanone.

2-bromo-1-(2,3-dihydro-2-methyl-1H-inden-2-yl)ethanone:

MS: 254 and 252 (2 and 2, M$^{+\cdot}$), 239 and 237 (0.5 and 0.5, M—CH$_3$), 173 (100, M—Br), 159 (39, M—CH$_2$Br), 155 (13), 145 (30), 143 (10), 131 (97, M—COCH$_2$Br), 130 (30), 129 (40), 128 (34), 127 (19), 116 (29), 115 (69), 91 (50), 77 (12), 63 (10), 43 (22).

(e)

4(5)-(2,3-Dihydro-2-methyl-1H-inden-2-yl)imidazole

4(5)-(2,3-Dihydro-2-methyl-1H-inden-2-yl)imidazole is prepared by the reaction of 2-bromo-1-(2,3-dihydro-2-methyl-1H-inden-2-yl)ethanone (2.04 g) with formamide (60 ml) as described in Example 6, method Af. Purification of the crude base via flash chromatography (methylene cloride/methanol 9.75/0.25) gave pure 4(5)-(2,3-dihydro-2-methyl-1H-inden-2-yl)imidazole. M.p. of the base 167°-170° C.

The base of 4(5)-(2,3-dihydro-2-methyl-1H-inden-2-yl)imidazole:

MS: 198 (44, M$^{+\cdot}$), 197 (13, M—H), 183 (100, M—CH$_3$), 129 (14), 128 (18), 115 (22), 91 (28), 77 (11).

$^1$H NMR (80 MHz, CDCl$_3$): δ1.48 (3H, s, CH$_3$), AB quartet: δ$_A$ 2.98, δ$_B$ 3.32, J$_{AB}$, 15.39 Hz (4H, 2x CH$_2$), 6.78 (1H, s, im-5(4)), 7.16 (4H, s, aromatic), 7.54 (1H, s, im-2), 8.74 (1H, s, >NH).

EXAMPLE 8

4(5)-(2,3-Dihydro-1H-inden-2-yl)imidazole (a)

2-Bromo-1-(2-bromo-2,3-dihydro-1H-inden-2-yl)ethanone

The procedure of Example 1(a) is repeated, except that the amount of bromine is doubled. After removal of the solvent the crude produce is used as such in step (b).

(b)

4(5)-(1H-Inden-2-yl)imidazole

The procedure of Example 1(b) is repeated. The product is recrystallized from methylene chloride.

(c)

4(5)-(2,3-Dihydro-1H-inden-2-yl)imidazole

The procedure of Example 2c is repeated except that 4(5)-(1H-inden-2-yl)imidazole is used in place of 4(5)-(2,3-dihydrobenzofuran-2-yl)imidazole. When the uptake of hydrogen ceases, the reaction mixture is filtered and the filtrate is made alkaline with sodium hydroxide. The separated oil is extracted into methylene chloride. The combined extracts are washed with water, dried over $Na_2SO_4$, and evaporated to dryness. The crude product is purified by converting it into the hydrochloride in ethyl acetate. M.p.: 184°–191° C.

EXAMPLE 9

4(5)-(2,3-Dihydro-5-methyl-1H-inden-2-yl)imidazole

The procedure of Example 8 is repeated except that in place of 1-(2,3-dihydro-1H-inden-2-yl)ethanone is used 1-(2,3-dihydro-5-methyl-1H-inden-2-yl)ethanone. M.p. (HCl): 171°–175° C.

$^1$H NMR (80 MHz, $CDCl_3$, as base): 2.3 (s, 3H), 2.8–3.8 (m, 5H), 6.8 (s, 1H), 7.0–7.1 (m, 3H), 7.5 (s, 1H), 9.9 (s, 1H).

EXAMPLE 10

4(5)-(2,3-Dihydro-2-ethyl-5-methyl-1H-inden-2-yl)imidazole

The procedure of Example 1 is repeated except that in place of 1-(2,3-dihydro-1H-inden-2-yl)ethanone is used 1-(2,3-dihydro-2-ethyl-5-methyl-1H-inden-2-yl)ethanone. M.p. 54°–57° C. as base.

MS: 226 (40%), 211 (12%), 197 (100%), 182 (7%), 128 (12%), 98 (17%), 84 (15%).

EXAMPLE 11

4(5)-(2,3-Dihydro-2-ethyl-1H-inden-2-yl)imidazole

The compound is prepared according to the procedure of Example 7 using 2,3-dihydro-1H-indene-2-carboxylic acid methyl ester and ethyl bromide as starting materials. M.p. (HCl): 211°–215° C.

$^1$H NMR (80 MHz, $CDCl_3$, as base): 0.78 (t, 3H), 1.88 (q, 2H), 3.17 (q, 4H), 6.75 (s, 1H), 7.13 (s, 4H), 7.53 (s, 1H), 10.01 (s, 1H).

EXAMPLE 12

4(5)-(2,3-Dihydro-2,5-dimethyl-1H-inden-2-yl)imidazole

The procedure of Example 1 is repeated except that in place of 1-(2,3-dihydro-1H-inden-2-yl)ethanone is used 1-(2,3-dihydro-2,5-dimethyl-1-H-inden-2-yl)ethanone. M.p.: 148°–151° C. as base.

$^1$H NMR (80 MHz, $CDCl_3$, as hydrochloride): 1.51 (s, 3H), 2.27 (s, 3H), AB quartet $\delta_A$ 3.04, $\delta_B$ 3.24 $J_{AB}$ 15.45 Hg (4H, 2x $CH_2$), 6.87–6.99 (m, 4H), 9.04 (s, 1H), 14 (broad band, 2H).

EXAMPLE 13

4(5)-(2,3-Dihydro-1H-inden-2-yl)imidazole (a)

2,3-Dihydro-1H-inden-2-yl glyoxal diethyl acetal 0.73 g of magnesium turnings are covered with 90 ml of dry diethylether. To that mixture is then added 6 g of 2-bromoindane in 20 ml of dry diethylether at such a rate that a gentle boiling is maintained. When the magnesium turnings have reacted the solution containing the Grignard reagent is cooled to room temperature. The reaction mixture is then added dropwise, over a period of 3 hours, to a cooled (0°–5° C. solution of diethoxyacetic acid piperidinyl amide (6.4 g) in 20 ml of dry diethylether. After the addition is complete, the reaction mixture is stirred for two hours at about 5° C. The mixture is then poured into a cold 2% sulfuric acid solution (50 ml). The solution is extracted with ether and the combined ether extracts are washed with water and evaporated to dryness to give a residue of crude product, which is used without purification in step (b).

(b)

1,1-Diethoxy-2-hydroxy-2-(2,3-dihydro-1H-inden-2-yl)ethane 4 g of crude 2,3-dihydro-1H-inden-2-yl glyoxal diethyl acetal is dissolved in 20 ml of ethanol and 3.8 g of sodium borohydride is added in small portions at a temperature below 30° C. After the addition is complete, the mixture is stirred overnight at room temperature. About 15 ml of ethanol is distilled off and 30 ml of water is added. The solution is extracted with methylene chloride. The combined methyle chloride extracts are washed with water, dried with sodium sulfate, and evaporated to dryness. The yield is about 4 g of oil, which is used directly in step (c).

(c)

4(5)-(2,3-Dihydro-1H-inden-2-yl)imidazole 4 g of the oil from the preceding step and 15 ml of formamide are combined and stirred at 150° C. while passing ammonia gas into the solution for 6 hours. The mixture is cooled to room temperature and 40 ml of water is added. Concentrated hydrochloric acid is added with cooling until the pH is 3–4.

The solution is washed with toluene, cooled and the pH is adjusted to 10–12 with 20% sodium hydroxide solution. The mixture is extracted with methylene chloride and the combined methylene chloride extracts are extracted with 10% acetic acid solution. The combined acetic acide extracts are made alkaline (pH 10–12) with 20% sodium hydroxide solution. The product is extracted into chloroform, and the combined chloroform extracts washed with water and dried with sodium sulfate. The solution is evaporated to dryness to give the product as base.

The hydrochloride is prepared by dissolving the base in ethyl acetate and adding HCl-ethyl acetate until pH is about 4. The mixture is cooled and filtered and the filter cake washed with a small amount of ethyl acetate. M.p. 185°-193° C.

EXAMPLE 14

4(5)-(1,2,3,4-Tetrahydronaphth-2-yl)imidazole

The starting material, 1-(1,2,3,4-tetrahydronaphth-2-yl)ethanone can be prepared from 1,2,3,4-tetrahydro-2-naphthoic acid chloride for example by the procedure of Newman, M. S. and Mangham, J. R. (*J. Am. Chem. Soc.* 71 (1949) 3342) or as described in this patent for many acid chlorides to afford the acetyl derivatives.

(a)

The mixture of
2-bromo-1-(1,2,3,4-tetrahydronaphth-2-yl)ethanone and 2-bromo-1-(2-bromo-1,2,3,4-tetrahydronaphth-2-yl)ethanone Bromination of 1-(1,2,3,4-tetrahydronaphth-2-yl)ethanone (3.00 g) in methylene chloride with bromide (2.75 g)/methylene chloride (10 ml) by the normal procedure described for example in Example 5 affords the mixture of 2-bromo-1-(1,2,3,4-tetrahydronaphth-2-yl)ethanone and 2-bromo-1-(2-bromo-1,2,3,4-tetrahydronaphth-2-yl)ethanone.

2-bromo-1-(1,2,3,4-tetrahydronaphth-2-yl)ethanone:
MS: 254 and 252 (14 and 14, M+·), 173 (54, M—Br), 159 (21, M—$CH_2$Br), 150 (11), 145 (25), 131 (46, M—$COCH_2$Br), 130 (23), 129 (100), 128 (27), 127 (12), 116 (12), 115 (26), 91 (16).

2-bromo-1-(2-bromo-1,2,3,4-tetrahydronaphth-2-yl)ethanone: MS: 334, 332 and 330 (invisible, M+·), 253 and 251 (96 and 100, M—Br), 172 (32, M—Br—Br), 157 (11), 153 (14), 130 (25, M—Br—$COCH_2$Br), 129 (81), 128 (56), 127 (22), 115 (20).

(b)

4(5)-(1,2,3,4-Tetrahydronaphth-2-yl)imidazole

The mixture of 2-bromo-1-(1,2,3,4-tetrahydronaphth-2-yl)ethanone and 2-bromo-1-(2-bromo-1,2,3,4-tetrahydronaphth-2-yl)ethanone is heated with formamide as in the case of Example 4d to afford a mixture of 4(5)-(1,2,3,4-tetrahydronaphth-2-yl)imidazole and probably both 4(5)-(1,4-dihydronaphth-2-yl)imidazole and 4(5)-(3,4-dihydronaphth-2-yl)imidazole. This mixture is directly hydrated at about 70° C. as in Example 4e to provide crude 4(5)-(1,2,3,4-tetrahydronaphth-2-yl)imidazole. The product as base is purified by flash chromatography (solvent system: methylene chloride/methanol 9.5/0.5). M.p. of the hydrochloride salt of 4(5)-(1,2,3,4-tetrahydronaphth-2-yl)imidazole 168°-177° C.

The hydrochloride salt of 4(5)-(1,2,3,4-tetrahydronaphth-2-yl)imidazole:
MS: 198 (100, M+·), 197 (64), 183 (31), 170 (22), 169 (30), 130 (22), 129 (18), 128 (23), 117 (16), 116 (10), 115 (30), 104 (77), 103 (23), 98 (12), 94 (12), 91 (16), 82 (30), 81 (15).

$^1$H NMR (80 MHz, MeOH-d$_4$): δ1.66-2.46 (2H, m, —$CH_2$$CH_2$CH), 2.86-3.13 (5H, m, 2x Ar$CH_2$ and —$CH_2$$CH$CH$_2$), 7.11 (4H, s, aromatic), 7.34 (1H, m, im-5(4)), 8.85 (1H, d, $^4$J 1.54 Hz, im-2).

$^{13}$C NMR (20 MHz, MeOH-d$_4$): δ29.23 (OFR t), 29.63 (t), 32.53 (d), 35.50 (t), 115.84 (d), 126.89 (d), 127.19 (d), 129.92 (2d), 134.70 (s), 135.43 (s), 136.52 (s), 139.45 (s).

EXAMPLE 15

4(5)-(2-Ethyl-1,2,3,4-tetrahydronaphth-2-yl)imidazole

(a)

2-Ethyl-1,2,3,4-tetrahydro-2-naphthoic acid methyl ester 1,2,3,4-Tetrahydro-2-napthoic acid methyl ester (prepared by the methylation of 1,2,3,4-tetrahydro-2-naphthoic acid) is converted to 2-ethyl-1,2,3,4-tetrahydro-2-naphthoic acid methyl ester by the procedure of Rathke, M. V. and Lindert, A. (*J. Am. Chem. Soc.* 93 (1971) 2318). B.p. 90°-95° C./0.3 mmHg. Yield 88%.

1,2,3,4-Tetrahydro-2-naphthoic acid methyl ester:
$^1$H NMR (80 MHz, CDCl$_3$): δ0.88 (3H, t, J 7.69 Hz, —$CH_2$$CH_3$), 1.53-3.34 (8H, m, —$CH_2$CH$_3$ and the methylene protons of the ring), 3.64 (3H, s, COO$CH_3$), 7.07 (4H, s, aromatic).

$^{13}$C NMR (20 MHz, CDCl$_3$): δ8.77 (OFR q), 26.26 (t), 30.23 (t), 31.05 (t), 36.83 (t), 46.09 (s), 51.51 (q), 125.62 (2d), 128.52 (d), 129.07 (d), 134.91 (s), 135.37 (s), 176.66 (s).

(b)

2-Ethyl-1,2,3,4-tetrahydro-2-naphthoic acid

The mixture of 2-ethyl-1,2,3,4-tetrahydro-2-naphthoic acid methyl ester (32.3 g), sodium hydroxide (32.3 g), ethanol (450 ml) and water (323 ml) is refluxed for 8 hr. Ethanol is largely distilled in vacuo, the residue diluted with water and washed with ether. The aqueous solution gives an acidification with hydrochloric acid the desired 2-ethyl-1,2,3,4-tetrahydro-2-naphthoic acid. The product is filterd. Yield 22.2 g, 73%.

2-Ethyl-1,2,3,4-tetrahydro-2-naphthoic acid:
$^1$H NMR (80 MHz, CDCl$_3$): δ0.83 (3H, t, J 7.69 Hz, —$CH_2$$CH_3$), 1.55-3.33 (8H, m, —$CH_2$CH$_3$ and the methylene protons of the ring), 7.07 (3H, s, aromatic), 11.45 (1H, broad s, —COOH).

$^{13}$C NMR (20 MHz, CDCl$_3$): δ8.75 (OFR q), 26,19 (t), 29.94 (t), 30.91 (t), 36.54 (t), 45.89 (s), 125.75 (2d), 128.63 (d), 129.14 (d), 134.68 (s), 135.35 (s), 183.06 (s).

(c)

2-Ethyl-1,2,3,4-tetrahydro-2-naphthoic acid chloride

A mixture of 2-ethyl-1,2,3,4-tetrahydro-2-naphthoic acid (22,0 g) and thionyl chloride is boiled for 5 days. The acid chloride is distilled. B.p. 110°-115° C./0.2 mmHg. Yield 21.6 g, 90%.

2-Ethyl-1,2,3,4-tetrahydro-2-naphthoic acid chloride:
$^1$H NMR (80 MHz, CDCl$_3$): δ0.97 (3H, t, J 7.69 Hz, —$CH_2$$CH_3$), 1.67-3.38 (8H, m, —$CH_2$CH$_3$ and the methylene protons of the ring), 7.10 (4H, s, aromatic).

$^{13}$C NMR (20 MHz, CDCl$_3$): δ8.36 (OFR q), 26.00 (t), 30.70 (t), 30.79 (t), 37.11 (t), 56.67 (s), 126.05 (d), 126.24 (d), 128.66 (d), 129.08 (d), 133.38 (s), 134.65 (s), 178.46 (s).

(d)

1-(2-Ethyl-1,2,3,4-tetrahydronaphth-2-yl)ethanone

2-Ethyl-1,2,3,4-tetrahydro-2-naphthoic acid chloride is converted to 1-(2-ethyl-1,2,3,4-tetrahydronaphth-2-yl)ethanone by the procedure described for example in Example 4b.

(e)

2-Bromo-1-(2-ethyl-1,2,3,4-tetrahydronaphth-2-yl)ethanone

Bromination of 1-(2-ethyl-1,2,3,4-tetrahydronaphth-2-yl)ethanone by the procedure of Example 7d yields 2-bromo-1-(2-ethyl-1,2,3,4-tetrahydronaphth-2-yl)ethanone.

2-Bromo-1-(2-ethyl-1,2,3,4-tetrahydronaphth-2-yl)ethanone:

MS: 282 and 280 (4 and 4, M+·), 253 and 251 (8 and 8, M—$CH_2CH_3$), 201 (20, M—Br), 187 (28, M—$CH_2Br$), 159 (22, M—$COCH_2$), 157 (12), 145 (30), 131 (10), 130 (12), 129 (50), 128 (32), 127 (14), 117 (100), 115 (30), 91 (21), 77 (10), 43 (24).

(f)

4(5)-(2-Ethyl-1,2,3,4-tetrahydronaphth-2-yl)imidazole

2-Bromo-1-(2-ethyl-1,2,3,4-tetrahydronaphth-2-yl)ethanone is converted to 4(5)-(2-ethyl-1,2,3,4-tetrahydronaphth-2-yl)imidazole by the procedure of Example 7e. M.p. of the hydrochloride salt 148°–156° C.

The hydrochloride salt of 4(5)-(2-ethyl-1,2,3,4-tetrahydronaphth-2-yl)imidazole:

MS: 226 (63, M·+), 211 (17, M—$CH_3$), 198 (25), 197 (100, M—$CH_2CH_3$), 195 (17), 129 (15), 128 (12), 115 (13), 104 (20), 98 (14), 82 (19), 81 (30), 69 (11).

$^1$H NMR (80 MHz, MeOH-$d_4$): δ 0.79 (3H, t, J 7.52 Hz, —$CH_2\underline{CH_3}$), 1.63–3.34 (8H, m, —$\underline{CH_2}CH_3$ and the methylene protons of the ring). 7.02–7.14 (5H, m, aromatic and im-4), 8.74 (1H, d, $^4$J 1.37 Hz, im-2).

$^{13}$C NMR (20 MHz, MeOH-$d_4$): δ 8.48 (OFR q), 26.70 (t), 33.30 (t), 34.00 (t), 38.54 (s), 39.48 (t), 117.91 (d), 126.99 (d), 127.11 (d), 129.66 (d), 130.14 (d), 135.02 (s), 135.20 (d), 136.20 (s), 140.40 (s).

EXAMPLE 16

4(5)-(2,3-Dihydro-2-ethyl-1-methyl-1H-inden-2-yl)imidazole

(a)

cis-2,3-Dihydro-1-methyl-1H-indene-2-carboxylic acid methyl ester cis-2,3-Dihydro-1-methyl-1H-indene-2-carboxylic acid methyl ester is prepared from cis-2,3-dihydro-1-methyl-1H-indene-2-carboxylic acid (see Example 4) by the standard methods using methanol and concentrated sulphuric acid. Yield 91%.

cis-2,3-Dihydro-1-methyl-1H-indene-2-carboxylic acid methyl ester:

$^1$H NMR (80 MHz, CDCl$_3$): δ 1.14 (3H, d, J 6.84 Hz, CH$\underline{CH_3}$), 2.76–3.66 (4H, m, H$^1$, H$^2$ and H$_2{}^3$ of the indane ring), 3.72 (3H, s, —COO$\underline{CH_3}$), 7.17 (4H, s, aromatic).

$^{13}$C NMR (20 MHz, CDCl$_3$): δ 17.01 (OFR q), 33.21 (t), 41.93 (d), 48.53 (d), 51.37 (q), 123.481 (d), 124.45 (d), 126.66 (d), 126.81 (d), 140.92 (s), 146.76 (s), 173.98 (s).

(b)

2,3-Dihydro-2-ethyl-1-methyl-1H-indene-2-carboxylic acid methyl ester 2,3-Dihydro-2-ethyl-1-methyl-1H-indene-2-carboxylic acid methyl ester is prepared by the procedure of Bathke, M. V. and Lindert, A. (*J. Am. Chem. Soc.* 93 (1971) 2318). B.p. 90°–95° C./0.3 mmHg. Yield 51%.

The product is probably the mixture of two isomers (cis the major isomer, trans the minor isomer).

2,3-Dihydro-2-ethyl-1-methyl-1H-indene-2-carboxylic acid methyl ester (the cis-isomer):

$^1$H NMR (80 MHz, CDCl$_3$): δ 0.86 (3H, t, J 7.18 Hz —$CH_2\underline{CH_3}$), 1.122 (3H, d, J 7.18 Hz, >CH$\underline{CH_3}$), 1.25–2.18 (2H, m, —$\underline{CH_2}CH_3$), 3.10 (1H, q, J 7.18 Hz, >$\underline{CH}CH_3$), AB quartet: $D_A$ 2.82, $D_B$ 3.52, $J_{AB}$ 16.41 Hz (2H, H$_2{}^3$ of the indane ring), 3.70 (3H, s, COO$CH_3$), 7.15 (4H, s, aromatic).

$^{13}$C NMR (20 MHz, CDCl$_3$): δ 9.84 (OFR q), 17.53 (q), 30.76 (t), 36.99 (t), 49.77 (d), 51.28 (q), 59.27 (s), 123.60 (d), 124.60 (d), 126.45 (d), 126.63 (d), 140.74 (s), 146.52 (s), 175.52 (s).

(c)

2,3-Dihydro-2-ethyl-1-methyl-1H-indene-2-carboxylic acid 2,3-Dihydro-2-ethyl-1-methyl-1H-indene-2-carboxylic acid is synthesized by the method of Example 15b. Yield 97%.

2,3-Dihydro-2-ethyl-1-methyl-1H-indene-2-carboxylic acid (the cis-isomer):

$^1$H NMR (80 MHz, CDCl$_3$): δ 0.93 (3H, t, J 7.18 Hz —$CH_2\underline{CH_3}$), 1.23 (3H, d, J 7.18 Hz, >CH$\underline{CH_3}$), 1.32–2.23 (2H, m, —$\underline{CH_2}CH_3$), 3.13 (1H, q, J 7.18 Hz, >$\underline{CH}CH_3$), AB quartet: $D_A$ 2.83, $D_B$ 3.49, $J_{AB}$ 16.21 Hz (2H, H$_2{}^3$ of the indane ring), 7.15 (4H, s, aromatic), 10.70 (1H, broad s, —COOH).

$^{13}$C NMR (20 MHz, CDCl$_3$): δ 9.81 (OFR q), 17.26 (q), 30.64 (t), 36.90 (t), 49.59 (d), 59.12 (s), 123.57 (d), 124.57 (d), 126.54 (d), 126.72 (d), 140.59 (s), 146.25 (s), 181.79 (s).

(d)

2,3-Dihydro-2-ethyl-1-methyl-1H-indene-2-carboxylic acid chloride 2,3-Dihydro-2-ethyl-1-methyl-1H-indene-2-carboxylic acid chloride is prepared by the standard method using thionyl chloride and has the boiling point 105° C./0.3 mmHg. Yield 94%.

2,3-Dihydro-2-ethyl-1-methyl-1H-indene-2-carboxylic acid chloride (the cis-isomer):

$^1$H NMR (80 MHz, CDCl$_3$): δ 0.95 (3H, t, J 7.18 Hz —$CH_2\underline{CH_3}$), 1.28 (3H, d, J 7.01 Hz, >CH$\underline{CH_3}$), 1.40–2.31 (2H, m, —$\underline{CH_2}CH_3$), 3.18 (1H, q, J 7.01 Hz, >$\underline{CH}CH_3$), AB quartet: $D_A$ 3.50, $J_{AB}$ 16.24 Hz (2H, H$_2{}^3$ of the indane ring), 7.17 (4H, s, aromatic).

$^{13}$C NMR (20 MHz, CDCl$_3$): δ 9.38 (OFR q), 17.86 (q), 30.88 (t), 36.60 (t), 49.74 (d), 68.75 (s), 123.75 (d), 124.87 (d), 127.02 (2d), 139.07 (s), 145.61 (s), 177.21 (s).

(e)

1-(2,3-Dihydro-2-ethyl-1-methyl-1H-inden-2-yl)ethanone 1-(2,3-Dihydro-2-ethyl-1-methyl-1H-inden-2-yl)ethanone is synthesized by the method of Example 4b. Yield 69%.

1-(2,3-Dihydro-2-ethyl-1-methyl-1H-inden-2-yl)ethanone (the cis-isomer):

$^1$H NMR (80 MHz, CDCl$_3$): δ 0.81 (3H, t, J 7.18 Hz —$CH_2\underline{CH_3}$), 1.06 (3H, d, J 7.18 Hz, >CH$\underline{CH_3}$), about 1.2–2.2 (2H, m, —$\underline{CH_2}CH_3$), 2.10 (3H, s, CO$\underline{CH_3}$), 3.10 (1H, q, J 7.18 Hz, >$\underline{CH}CH_3$), AB quartet: $D_A$ 2.75, $D_B$ 3.45, $J_{AB}$ 16.41 Hz (2H, H$_2{}^3$ of the indane ring), 7.15 (4H, s, aromatic).

$^{13}$C NMR (20 MHz, CDCl$_3$): δ 9.60 (OFR q), 17.35 (q), 27.55 (q), 29.82 (t), 35.33 (t), 49.04 (d), 64.93 (s), 123.60 (d), 124.87 (d), 126.60 (d), 126.75 (d), 140.80 (s), 146.67 (s), 210.85 (s).

(f)

2-Bromo-1-(2,3-dihydro-2-ethyl-1-methyl-1H-inden-2-yl)ethanone

2-Bromo-1-(2,3-dihydro-2-ethyl-1-methyl-1H-inden-2-yl)ethanone is prepared from 1-(2,3-dihydro-2-ethyl-1-methyl-1H-inden-2-yl)ethanone (21.6 g) by treatment with bromine (17.6 g) in methylene chloride (300 ml). Yield 65%.

(g)

4(5)-(2,3-Dihydro-2-ethyl-1-methyl-1H-inden-2-yl)imidazole

The procedure of Example 1b is used to synthesize 4(5)-(2,3-dihydro-2-ethyl-1-methyl-1H-inden-2-yl)imidazole. Yield 28%. The base obtained is covered to its hydrochloride salt in dry ether. The hydrochloride salt is recrystallized from ethyl acetate-petroleum ether. The product is the mixture of two isomers, cis 85% and trans 15%. The melting point of the hydrochloride salt is 154°–158° C.

The hydrochloride salt of 4(5)-(2,3-dihydro-2-ethyl-1-methyl-1H-inden-2-yl)imidazole (the mixture of the cis- and transisomer, 85% and 15%):

MS: 226 (30, M$^{+\cdot}$), 211 (15, M—CH$_3$), 197 (100, M—CH$_2$CH$_3$), 182 (10), 129 (10), 128 (10), 115 (10), 91 (12). $^1$H NMR (80 MHz, MeOH-d$_4$): δ 0.79 (3H, distorted t, $^3$J 7.35 Hz —CH$_2$CH$_3$), 0.95 (3H, d, $^3$J 7.18 Hz, >CHCH$_3$, the cis-isomer), 1.28 (d, J 7.18 Hz, >CHCH$_3$, the trans-isomer), 1.47–2.27 (2H, m, —CH$_2$CH$_3$), 2.99–3.48 (3H, m, H$^1$ and H$_2$$^3$ protons of the indane ring). 7.14–7.31 (5H, m, aromatic and im-4(5)), 8.90 (1H, d, $^4$J 1.54 Hz, im-5).

The cis-isomer $^{13}$C NMR (MeOH-d$_4$): δ 9.72 (OFR q), 16.47 (q), 31.91 (t), 40.69 (t), 51.31 (d), 52.49 (s), 118.24 (d), 124.75 (d), 125.48 (d), 128.02 (2d), 135.08 (d), 138.83 (s), 141.10 (s), 147.70 (s).

EXAMPLE 17

4(5)-(2,3-Dihydro-2-n-propyl-1H-inden-2-yl)imidazole

4(5)-(2,3-Dihydro-2-n-propyl-1H-inden-2-yl)imidazole is prepared according to the procedure of Example 7 using 2,3-dihydro-1H-indene-2-carboxylic acid methyl ester and n-propyl bromide as starting materials. M.p. of the hydrochloride salt: 169°–171° C.

The hydrochloride salt of 4(5)-(2,3-dihydro-2-n-propyl-1H-inden-2-yl)imidazole:

MS: 226 (25, M$^{+\cdot}$), 197 (17, M—CH$_2$CH$_3$), 183 (100, M—CH$_2$CH$_2$CH$_3$), 115 (13), 91 (17).

$^1$H NMR (80 MHz, MeOH-d$_4$): δ 0.79–1.31 (5H, m, 0.88 distorted t, CH$_2$CH$_3$), 1.79 –1.99 (2H, m, CH$_2$CH$_2$CH$_3$), AB quartet: D$_A$=D$_B$ 3.23, J$_{AB}$ 16.4 Hz (4H, H$_2$$^1$ and H$_2$$^3$ of the indane ring), 7.05–7.25 (4H, m, aromatic), 7.31 (1H, d, $^4$J 1.4 Hz, im-5(4)), 8.82 (1H, d, im-2, $^4$J 1.4 Hz).

EXAMPLE 18

4(5)-(2,3-Dihydro-2-n-butyl-1H-inden-2-yl)imidazole

4(5)-(2,3-Dihydro-2-n-butyl-1H-inden-2-yl)imidazole is prepared according to the procedure of Example 7 using 2,3-dihydro-1H-indene-2-carboxylic acid methyl ester and n-butyl bromide as starting materials. M.p. of the hydrochloride salt: 129°–132° C.

The hydrochloride salt of 4(5)-(2,3-dihydro-2-n-butyl-1H-inden-2-yl)imidazole:

MS: 240 (22, M$^{+\cdot}$), 197 (12, M—CH$_2$CH$_2$CH$_3$), 183 (100, M—CH$_2$CH$_2$—CH$_2$CH$_3$), 170 (24), 141 (23), 129 (10), 128 (10), 115 (15), 97 (11), 91 (17), 81 (16), 77 (38), 69 (16), 57 (18), 55 (17), 51 (10).

$^1$H NMR (80 MHz, MeOH-d$_4$): δ 0.86 (3H, distorted t, CH$_3$), 1.00–1.50 (4H, m, CH$_2$CH$_2$CH$_3$), 1.81–2.00 (2H, m, CH$_2$CH$_2$CH$_2$CH$_3$), AB quartet: D$_A$=D$_B$ 3.23, J$_{AB}$ 16.4 Hz (4H, H$_2$$^1$ and H$_2$$^3$ protons of the indane ring), 7.05–7.25 (4H, m, aromatic), 7.31 (1H, d, $^4$J 1.4 Hz, im-5(4)), 8.81 (1H, d, $^4$J 1.4 Hz, im-2).

EXAMPLE 19

4(5)-(2,3-Dihydro-2-ethyl-1-hydroxy-1H-inden-2-yl)imidazole (a)

4(5)-(2,3-Dihydro-2-ethyl-1-oxo-1H-inden-2-yl)imidazole

2-Acetyl-1-indanone (Liebigs Ann. Chem. 347 (1906) 112) is alkylated with ethylbromide in acetone in the presence of sodiumcarbonate to 2-acetyl-2-ethyl-1-indanone. The acetyl group is brominated with bromine in methanol and to imidazole by heating in formamide as before. The melting point of the product as base is 126°–127° C. (from ethyl acetate).

(b)

4(5)-2,3-Dihydro-2-ethyl-1-hydroxy-1H-inden-2-yl)imidazole

The carbonyl gorup of oxo inden imidazole from the step (a) is reduced to the alcohol group with sodium borohydride in ethanol. The product is the mixture of cis-trans stereoisomers, the purification of which is accomplished by liquid chromatography.

cis-isomer as hydrochloride (m.p. 184°–185° C.):
$^1$H NMR (80 MHz, MeOH-d$_4$): 0.73 (3H, t), 1.86 (2H, m), 3.36 (2H, m), 3.61 (3H, s), 5.15 (1H, s), 7.06 (1H, d), 7.2–7.4 (4H, m), 8.69 (1H, d), trans-isomer as hydrochloride:
$^1$H NMR (80 MHz, MeOH-d$_4$): 0.80 (3H, t), 1.84 (2H, m), 3.15 (2H, m), 3.24 (3H, s), 5.15 (1H, s), 6.87 (1H, d), 7.2–7.4 (4H, m), 8.54 (1H, d),

EXAMPLE 20

4(5)-(2,3-Dihydro-2-ethyl-1H-inden-2-yl)-imidazole

The oxo derivative prepared in the example 19 (step a) or the hydroxy derivative (step b) is hydrogenated in 2N hydrochloric acid in the presence of 10% palladium on carbon at 70° C. When the uptake of hydrogen ceases, the reaction mixture is filtered and made alkaline. The product is extracted with methylene chloride which is washed with water, dried and evaporated to dryness. From the residue, which is the product as base, is made the hydrochloride using dry hydrogen chloride in ethyl acetate. It has M.p.: 211°–215° C.

We claim:

1. A substituted imidazole of the formula

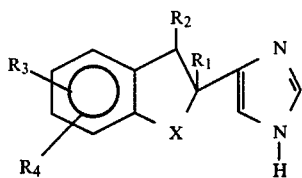 (I)

or a non-toxic acid addition salt thereof, wherein
X is —$CH_2$—, —$CH_2CH_2$— or —O—,
$R_1$ is H, alkyl of 1 to 4 carbon atoms, alkenyl of 2 to 4 carbon atoms,
$OCH_3$ or $OCH_2CH_3$,
$R_2$ is H, $CH_3$, $CH_2CH_3$, $OCH_3$ or OH,
$R_3$ is —H, $CH_3$, $CH_2CH_3$, $OCH_3$ or Hal,
$R_4$ is H, $CH_3$, $CH_2CH_3$, $OCH_3$ or Hal, and Hal is halogen.

2. An imidazole according to claim 1 wherein $R_1$ is hydrogen, $CH_3$, $CH_2CH_3$, $OCH_3$, or $OCH_2CH_3$.

3. An imidazole according to claim 2, wherein $R_1$ is hydrogen, $CH_3$, $CH_2CH_3$, $OCH_3$ or $OCH_2CH_3$, X is $CH_2$, and $R_2$, $R_3$ and $R_4$ are hydrogen.

4. An imidazole according to claim 1 which is 4(5)-(2,3-dihydro-1H-inden-2-yl)imidazole.

5. An imidazole according to claim 1 which is 4(5)-(2,3-dihydrobenzofuran-2-yl)imidazole.

6. An imidazole according to claim 1 which is 4(5)-(5-bromo-2,3-dihydrobenzofuran-2-yl)imidazole.

7. An imidazole according to claim 1 which is 4(5)-(2,3-dihydro-2-ethyl-5-methyl-1H-inden-2-yl)imidazole.

8. An imidazole according to claim 1 which is 4(5)-(2-ethyl-1,2,3,4-tetrahydronaphth-2-yl)imidazole.

9. An imidazole according to claim 1 which is 4(5)-(2,3-dihydro-2-ethyl-1-methyl-1H-inden-2-yl)imidazole.

10. An imidazole according to claim 1 which is 4(5)-(2,3-dihydro-2-n-propyl-1H-inden-2-yl)imidazole.

11. An imidazole according to claim 1 which is 4(5)-(2,3-dihydro-4-methy-1H-inden-2-yl)imidazole.

12. An imidazole according to claim 1 which is 4(5)-(2,3-dihydro-5-methyl-1H-inden-2-yl)imidazole.

13. An imidazole according to claim 1 which is 4(5)-(2,3-dihydro-1-methyl-1H-inden-2-yl)imidazole.

14. An imidazole according to claim 1 which is 4(5)-(2,3-dihydro-1,4-dimethyl-1H-inden-2-yl)imidazole.

15. An imidazole according to claim 1 which is 4(5)-(2,3-dihydro-1,6-dimethyl-1H-inden-2-yl)imidazole.

16. An imidazole according to claim 1 which is 4(5)-(5-chloro-2,3-dihydro-1H-inden-2-yl)imidazole.

17. An imidazole according to claim 1 which is 4(5)-(5-bromo-2,3-dihydro-1H-inden-2-yl)imidazole.

18. An imidazole according to claim 1 which is 4(5)-(2,3-dihydro-1-hydroxy-1H-inden-2-yl)imidazole.

19. An imidazole according to claim 1 which is 4(5)-(2,3-diydro-2-methyl-1H-inden-2-yl)imidazole.

20. An imidazole according to claim 1 which is 4(5)-(4-chloro-2,3-dihydro-1H-inden-2-yl)imidazole.

21. An imidazole according to claim 1 which is 4(5)-(4-bromo-2,3-dihydro-1H-inden-2-yl)imidazole.

22. An imidazole according to claim 1 which is 4(5)-(2,3-dihydro-2-ethyl-1H-inden-2-yl)imidazole.

23. An imidazole according to claim 1 which is 4(5)-(2,3-dihydro-2-n-butyl-1H-inden-2-yl)imidazole.

24. An imidazole according to claim 1 which is 4(5)-(2,3-dihydro-2,5-dimethyl-1H-inden-2-yl)imidazole.

25. An imidazole according to claim 1 which is 4(5)-(1,2,3,4-tetrahydronaphth-2-yl)imidazole.

26. An imidazole according to claim 1 which is 4(5)-(2,3-dihydro-2-ethyl-1-hydroxy-1H-inden-2-yl)imidazole.

27. A pharmaceutical composition useful to block $\alpha_2$-receptors comprising a substituted imidazole as claimed in claim 1 or a non-toxic acid addition salt thereof in an amount effective to produce said block, in association with a compatible pharmaceutically acceptable carrier.

28. Method of blocking $\alpha_2$-receptors which comprises administering to a subject in which said block is required an effective amount of a substituted imidazole as claimed in claim 1.

* * * * *

UNITED STATES PATENT AND TRADEMARK OFFICE

CERTIFICATE EXTENDING PATENT TERM
UNDER 35 U.S.C. § 156

PATENT NO.      :   4,689,339

ISSUED          :   August 25, 1987

INVENTOR(S)     :   Arto J. Karjalainen et al.

PATENT OWNER    :   Orion-Yhtymä Oy

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

1,719 days from November 21, 2005, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 15th day of July 1998.

Bruce A. Lehman
Assistant Secretary of Commerce and
Commissioner of Patents and Trademarks